US009509982B2

(12) United States Patent
Tsukagoshi et al.

(10) Patent No.: US 9,509,982 B2
(45) Date of Patent: Nov. 29, 2016

(54) IMAGE PROCESSING SYSTEM AND METHOD

(75) Inventors: Shinsuke Tsukagoshi, Nasushiobara (JP); Takumi Hara, Akishima (JP); Takahiro Yoda, Nasushiobara (JP); Tatsuo Maeda, Nasushiobara (JP); Masaharu Tsuyuki, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 773 days.

(21) Appl. No.: 13/495,557

(22) Filed: Jun. 13, 2012

(65) Prior Publication Data

US 2012/0320167 A1 Dec. 20, 2012

(30) Foreign Application Priority Data

Jun. 15, 2011 (JP) ................................. 2011-133164

(51) Int. Cl.

| H04N 15/00 | (2006.01) |
| H04N 9/47 | (2006.01) |
| H04N 13/04 | (2006.01) |
| H04N 13/00 | (2006.01) |
| G06F 19/00 | (2011.01) |
| A61B 6/00 | (2006.01) |

(52) U.S. Cl.
CPC ...... *H04N 13/0406* (2013.01); *H04N 13/0062* (2013.01); *H04N 13/0434* (2013.01); *H04N 13/0497* (2013.01); *A61B 6/466* (2013.01); *G06F 19/321* (2013.01)

(58) Field of Classification Search
USPC .................................................. 348/41–161
See application file for complete search history.

(56) References Cited

U.S. PATENT DOCUMENTS

| 6,285,368 B1* | 9/2001 | Sudo ...................... G09G 3/003 345/418 |
| 2002/0131625 A1* | 9/2002 | Vining .............. G06F 17/30256 382/128 |
| 2008/0158346 A1 | 7/2008 | Okamoto et al. |
| 2008/0247636 A1* | 10/2008 | Davis ...................... G06T 19/00 382/152 |

(Continued)

FOREIGN PATENT DOCUMENTS

| CN | 102036081 A | 4/2011 |
| EP | 0 860 807 A2 | 8/1998 |

(Continued)

OTHER PUBLICATIONS

Extended European Search Report issued Nov. 30, 2012, in European Patent Application No. 12172277.1.

(Continued)

*Primary Examiner* — Frederick Bailey
*Assistant Examiner* — Talha M Nawaz
(74) *Attorney, Agent, or Firm* — Oblon, McClelland, Maier & Neustadt, L.L.P.

(57) ABSTRACT

An image processing system according to an embodiment includes a display unit capable of displaying stereoscopic images by displaying a group of parallax images and a display control unit. The display control unit displays an operation screen for receiving operations on medical image data on the display unit, displays selection information for selecting medical image data on the operation screen, and controls whether the selection information will be displayed as a stereoscopic image or a planar image depending on the content of medical image data selected by the selection information.

6 Claims, 13 Drawing Sheets

(56) References Cited

U.S. PATENT DOCUMENTS

| | | | |
|---|---|---|---|
| 2008/0278573 A1* | 11/2008 | Ropinski | H04N 13/0404 348/51 |
| 2011/0044525 A1* | 2/2011 | Ohishi | A61B 6/4014 382/132 |
| 2011/0235066 A1* | 9/2011 | Sakuragi | G06T 7/0022 358/1.6 |
| 2012/0038625 A1* | 2/2012 | Kim | G06F 3/04815 345/419 |
| 2012/0282583 A1* | 11/2012 | Thaler | G09B 23/28 434/267 |
| 2013/0181977 A1* | 7/2013 | Tsukagoshi | G09G 5/14 345/419 |

FOREIGN PATENT DOCUMENTS

| | | |
|---|---|---|
| EP | 0 860 807 A3 | 8/1998 |
| EP | 2 306 748 A2 | 4/2011 |
| EP | 2 306 748 A3 | 4/2011 |
| EP | 2 375 756 A1 | 10/2011 |
| JP | 2002-101428 A | 4/2002 |
| JP | 2004-120165 A | 4/2004 |
| JP | 2004-357789 | 12/2004 |
| JP | 2005-86414 | 3/2005 |
| JP | 2009-131421 A | 6/2009 |
| JP | 2011-35827 A | 2/2011 |

OTHER PUBLICATIONS

Communication pursuant to Article 94(3) EPC issued Nov. 3, 2014 in European Patent Application No. 12 172 277.1.

Combined Office Action and Search Report issued Feb. 24, 2014 in Chinese Application No. 201210194988.0.

Japanese Office Action issued Jan. 20, 2015 in Patent Application No. 2011-133164 (without English Translation).

Office Action issued Oct. 6, 2015 in Japanese Patent Application No. 2011-133164.

Office Action issued on Apr. 4, 2016 in European Patent Application No. 12 172 277.1.

* cited by examiner

FIG.10

| IMAGING RANGE | THUMBNAIL ICON IMAGE |
|---|---|
| HEAD | HEAD.jpeg |
| CHEST | CHEST.jpeg |
| ABDOMEN | ABDOMEN.jpeg |
| LEG | LEG.jpeg |

FIG.11

| NUMBER | STEREOSCOPIC EFFECT |
|---|---|
| 1 | 0 |
| 2 TO 100 | 1 |
| ~200 | 2 |
| ~300 | 3 |
| ~400 | 4 |
| ~500 | 5 |
| MORE THAN THE ABOVE | 6 |

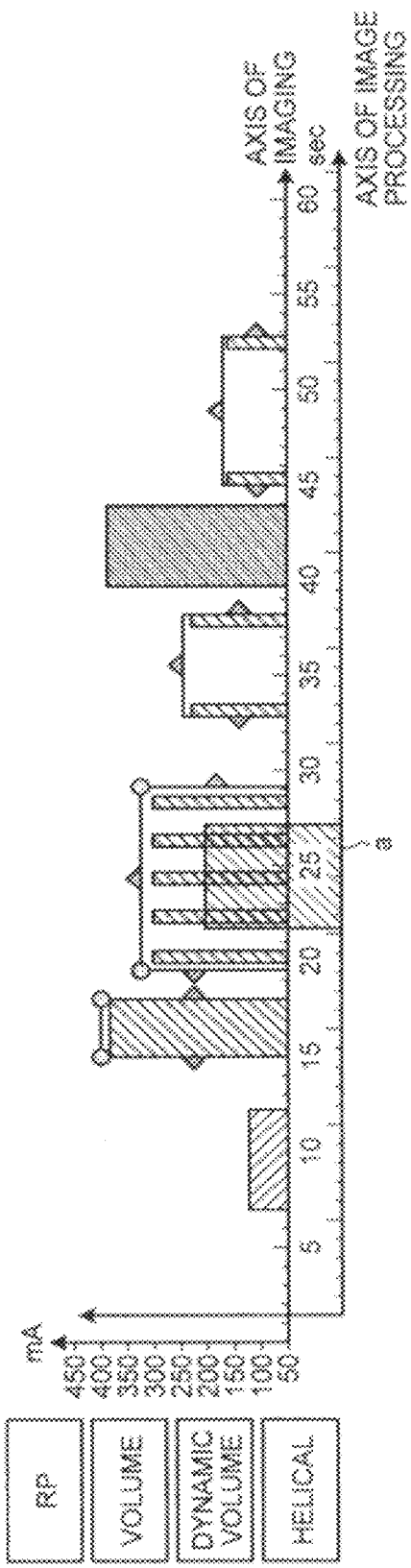

IMAGE PROCESSING SYSTEM AND METHOD

CROSS-REFERENCE TO RELATED APPLICATIONS

This application is based upon and claims the benefit of priority from Japanese Patent Application No. 2011-133164, filed on Jun. 15, 2011; the entire contents of which are incorporated herein by reference.

FIELD

Embodiments described herein relate generally to an image processing system and method.

BACKGROUND

In the past, apparatuses capable of generating 3-dimensional medical image data (hereinafter referred to as volume data) have been practically used as medical image diagnostic apparatuses such as an X-ray CT (computed tomography) apparatus, an MRI (magnetic resonance imaging) apparatus, or an ultrasonic diagnostic apparatus. The medical image diagnostic apparatus collects imaging data by imaging a subject and generates volume data by performing image processing on the collected imaging data. Moreover, the medical image diagnostic apparatus generates a display image to be displayed on a monitor by performing a volume rendering process on the generated volume data. Here, the medical image diagnostic apparatus displays an operation screen for receiving operations from an operator on a monitor in synchronization with imaging of a subject or generation or displaying of display images. Moreover, the medical image diagnostic apparatus performs imaging of a subject, generation or displaying of display images, and the like in accordance with an operation received on the operation screen.

On the other hand, in recent years, stereoscopic monitors which enable 2-parallax images imaged from two viewpoints to be perceived stereoscopically using a dedicated device such as stereoscopic glasses have been practically used. Moreover, stereoscopic monitors which enable multi-parallax images (for example, 9-parallax images) imaged from multiple viewpoints to be perceived stereoscopically with the naked eyes of a viewer by using a beam controller such as a lenticular lens have been practically used. The 2-parallax images or 9-parallax images displayed on the stereoscopic monitor are sometimes generated by estimating the depth information of images imaged from one viewpoint and performing image processing on the images using the estimated information.

BRIEF DESCRIPTION OF THE DRAWINGS

FIG. 10 is a diagram for describing generation of a thumbnail region according to the first embodiment;

FIG. 11 is a diagram for describing generation of a thumbnail region according to the first embodiment;

FIG. 18 is a diagram for describing a time schedule screen according to a third embodiment.

DETAILED DESCRIPTION

An image processing system according to an embodiment includes a display unit capable of displaying stereoscopic images by displaying a group of parallax images and a display control unit. The display control unit displays an operation screen for receiving operations on medical image data on the display unit, displays selection information for selecting medical image data on the operation screen, and controls whether the selection information will be displayed as a stereoscopic image or a planar image depending on the content of medical image data selected by the selection information.

Hereinafter, embodiments of an image processing system and method will be described in detail with reference to the accompanying drawings. Some terms used in the following embodiments will be described. "A group of parallax images" is a group of images obtained by moving a viewpoint position at which an object is observed by a predetermined parallax angle. For example, "a group of parallax images" can be generated by performing a volume rendering process with respect to volume data with the viewpoint position moved by a predetermined parallax angle. Moreover, for example, "a group of parallax images" can be generated by performing a computation process so that a predetermined shape (for example, a cuboid) can be stereoscopically perceived. That is, "a group of parallax images" is made up of a plurality of "parallax images" having different "viewpoint positions." Moreover, "parallax angle" is an angle determined by adjacent viewpoint positions among the respective viewpoint positions set to generate the "a group of parallax images" and a predetermined position (for example, the center of a space) within a space represented by volume data. Moreover, "parallax number" is the number of "parallax images" necessary for the images to be perceived stereoscopically on a stereoscopic monitor. Moreover, "9-parallax image" described below is "a group of parallax images" made up of nine "parallax images." Moreover, "2-parallax image" described below is a "group of parallax images" made up of two "parallax images."

First Embodiment

Figure 1:
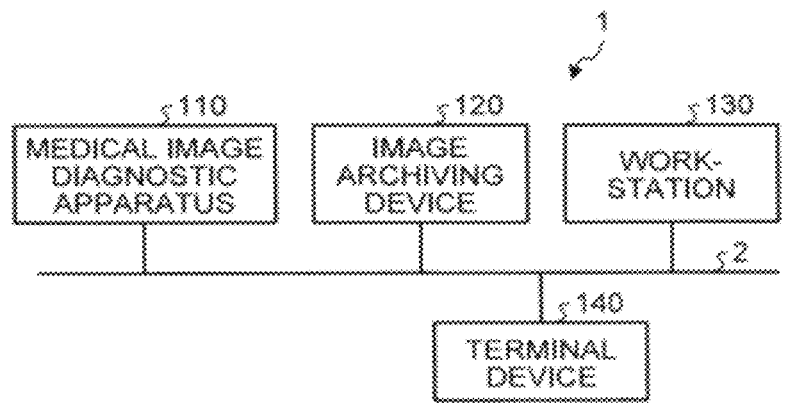
FIG. 1 is a diagram for describing a configuration example of an image processing system according to a first embodiment.

First, a configuration example of an image processing system according to the first embodiment will be described. FIG. 1 is a diagram for describing a configuration example of an image processing system according to the first embodiment.

As illustrated in FIG. 1, an image processing system 1 according to the first embodiment includes a medical image diagnostic apparatus 110, an image archiving device 120, a workstation 130, and a terminal device 140. The respective devices illustrated in FIG. 1 can communicate directly or indirectly with each other by a LAN (local area network) 2 installed in a hospital, for example. For example, when a PACS (picture archiving and communication system) is incorporated into the image processing system 1, the respective devices transmit and receive medical images or the like to and from the other devices in accordance with the DICOM (Digital Imaging and Communications in Medicine) standard.

The image processing system 1 generates a group of parallax images serving as display images from volume data which is 3-dimensional medical image data collected by the medical image diagnostic apparatus 110 and displays the group of parallax images on a stereoscopic monitor to thereby provide stereoscopic medical images to doctors and examiners working in a hospital. Specifically, in the first embodiment, the medical image diagnostic apparatus 110 performs various image processes with respect to volume data to generate a group of parallax images. Moreover, the medical image diagnostic apparatus 110, the workstation 130, and the terminal device 140 include stereoscopic monitors thereof, and the group of parallax images generated by the medical image diagnostic apparatus 110 is displayed on the monitors. Moreover, the image archiving device 120 archives the volume data and the group of parallax images generated by the medical image diagnostic apparatus 110. That is, the workstation 130 and the terminal device 140 acquire the group of parallax images from the image archiving device 120 and process the group of parallax images and display the same on the monitors. Moreover, in the first embodiment, the medical image diagnostic apparatus 110, the workstation 130, and the terminal device 140 display icons to be displayed on operation screens thereof so as to be perceived stereoscopically. Here, "icons" are information for receiving operations from an operator and are figures and characters, or a combination thereof, designed to enhance visibility. Hereinafter, respective devices will be described in order.

The medical image diagnostic apparatus 110 is an X-ray diagnostic apparatus, an X-ray CT (computed tomography) apparatus, an MRI (magnetic resonance imaging) apparatus, an ultrasonic diagnostic apparatus, a SPECT (single photon emission computed tomography) apparatus, a PET (positron emission computed tomography) apparatus, a SPECT-CT apparatus in which a SPECT apparatus and an X-ray CT apparatus are integrated, a PET-CT apparatus in which a PET apparatus and an X-ray CT apparatus are integrated, or a cluster of these apparatuses. Moreover, the medical image diagnostic apparatus 110 according to the first embodiment can generate 3-dimensional medical image data (volume data).

Specifically, the medical image diagnostic apparatus 110 according to the first embodiment generates volume data by imaging a subject. For example, the medical image diagnostic apparatus 110 collects imaging data such as projection data or MR signals by imaging a subject and generates volume data by reconstructing medical image data of a plurality of axial planes along the body axis direction of the subject from the collected imaging data. For example, the medical image diagnostic apparatus 110 reconstructs medical image data of 500 axial planes. A group of medical image data of the 500 axial planes is volume data. The projection data or the MR (magnetic resonance) signals themselves of the subject imaged by the medical image diagnostic apparatus 110 may be referred to as volume data.

Moreover, the medical image diagnostic apparatus 110 according to the first embodiment performs various rendering processes with respect to the generated volume data to generate a group of parallax images.

Moreover, the medical image diagnostic apparatus 110 according to the first embodiment includes a stereoscopic monitor (hereinafter, a stereoscopic display monitor) as a display unit. The medical image diagnostic apparatus 110 generates a group of parallax images and displays the generated group of parallax images on the stereoscopic display monitor. As a result, the operator of the medical image diagnostic apparatus 110 can perform an operation for generating the group of parallax images while checking stereoscopic medical images displayed on the stereoscopic display monitor.

Moreover, the medical image diagnostic apparatus 110 transmits the generated volume data and the generated group of parallax images to the image archiving device 120. When transmitting the volume data and the group of parallax images to the image archiving device 120, the medical image diagnostic apparatus 110 transmits additional information. Examples of the additional information include a patient ID for identifying a patient, an examination ID for identifying an examination, an apparatus ID for identifying the medical image diagnostic apparatus 110, and a series ID for identifying each imaging by the medical image diagnostic apparatus 110. Moreover, the additional information transmitted to the image archiving device 120 together with the group of parallax images includes additional information regarding the group of parallax images. Examples of the additional information regarding the group of parallax images include the number (for example, "9") of parallax image and a resolution (for example, "466×350 pixels") of a parallax image.

The image archiving device 120 is a database in which medical images are archived. Specifically, the image archiving device 120 according to the first embodiment stores the volume data and the group of parallax images transmitted from the medical image diagnostic apparatus 110 in a storage unit and archives the same. In the first embodiment, by using the workstation 130 capable of archiving a large volume of images, the workstation 130 and the image archiving device 120 illustrated in FIG. 1 may be integrated with each other. That is, in the first embodiment, the volume data and the group of parallax images may be stored in the workstation 130 itself.

In the first embodiment, the volume data and the group of parallax images archived in the image archiving device 120 are archived in correlation with a patient ID, an examination ID, an apparatus ID, a series ID, and the like. Thus, the workstation 130 and the terminal device 140 acquire necessary volume data and the necessary group of parallax images from the image archiving device 120 by retrieving the same using the patient ID, the examination ID, the apparatus ID, the series ID, and the like.

The workstation 130 is an image processing apparatus that performs image processing on medical images. Specifically, the workstation 130 according to the first embodiment acquires the group of parallax images acquired from the image archiving device 120 and displays the acquired group of parallax images on a stereoscopic display monitor. As a result, doctors and examiners who are viewers can view the stereoscopic medical images. In the first embodiment, although the medical image diagnostic apparatus 110 performs processes up to generation of the group of parallax images, for example, the workstation 130 according to the first embodiment may acquire volume data from the image archiving device 120, perform various rendering processes with respect to the acquired volume data, and generate the group of parallax images.

The terminal device 140 is a device for allowing doctors and examiners working in a hospital to view medical images. For example, the terminal device 140 is a PC (personal computer), a tablet PC, a PDA (personal digital assistant), a mobile phone, or the like, operated by doctors and examiners working in a hospital. Specifically, the terminal device 140 according to the first embodiment includes a stereoscopic display monitor as a display unit. Moreover, the terminal device 140 acquires a group of parallax images from the image archiving device 120 and displays the acquired group of parallax images on the stereoscopic display monitor. As a result, doctors and examiners who are viewers can view the stereoscopic medical images.

Here, the stereoscopic display monitor included in the medical image diagnostic apparatus 110, the workstation 130, and the terminal device 140 will be described. Most popular general-purpose monitors are configured to display 2-dimensional images in a 2-dimensional plane and are unable to display 2-dimensional images stereoscopically. If a viewer wants to view images stereoscopically on a general-purpose monitor, an apparatus that outputs images to the general-purpose monitor may need to display 2-parallax images in parallel which can be perceived stereoscopically by a viewer by a parallel viewing method or a cross-eyed viewing method. Alternatively, the apparatus that outputs images to the general-purpose monitor may need to display images which can be perceived stereoscopically by a viewer by a complementary color method using glasses in which a red cellophane is attached to the left-eye portion and a blue cellophane is attached to the right-eye portion.

On the other hand, an example of the stereoscopic display monitor is known, such as a stereoscopic display monitor which enables 2-parallax images (also referred to as binocular parallax images) to be perceived stereoscopically using dedicated devices such as stereoscopic glasses.

Figure 2A:
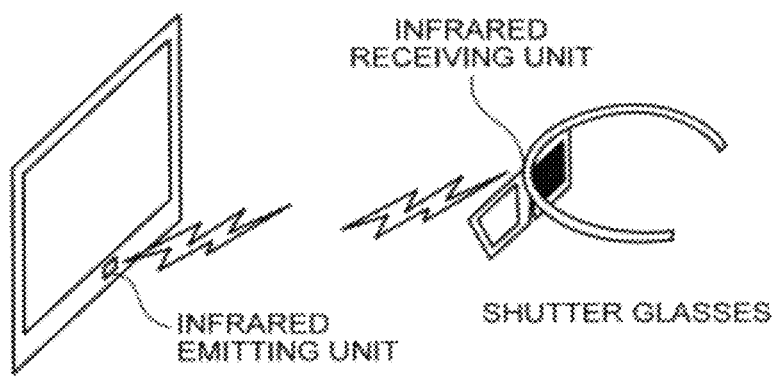
FIGS. 2A and 2B are diagrams for describing an example of a stereoscopic display monitor that performs stereoscopic display using 2-parallax images.
Figure 2B:
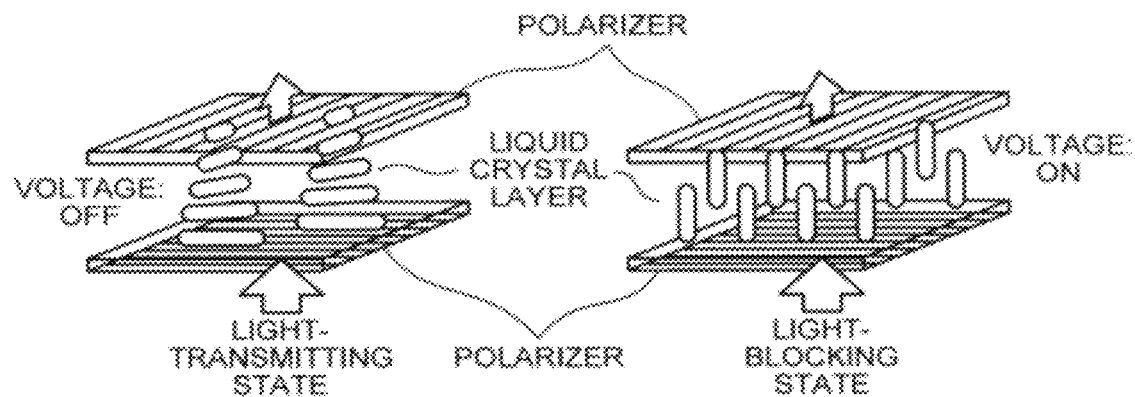

FIGS. 2A and 2B are diagrams for describing an example of a stereoscopic display monitor which performs stereoscopic display using 2-parallax images. The example illustrated in FIGS. 2A and 2B is a stereoscopic display monitor that performs stereoscopic display by a shutter method, and shutter glasses are used as stereoscopic glasses worn by a viewer who watches the monitor. The stereoscopic display monitor alternately outputs 2-parallax images on the monitor. For example, the monitor illustrated in FIG. 2A alternately outputs a left-eye image and a right-eye image at a frequency of 120 Hz. As illustrated in FIG. 2A, an infrared emitting unit is provided in the monitor, and the infrared emitting unit controls the emission of infrared light in accordance with an image switching timing.

Moreover, the infrared light emitted from the infrared emitting unit is received by an infrared receiving unit of the shutter glasses illustrated in FIG. 2A. A shutter is included in each of the left and right frames of the shutter glasses, and the shutter glasses alternately switch between a light-transmitting state and a light-blocking state of the left and right shutters in accordance with the timing at which infrared light is received by the infrared receiving unit. Hereinafter, a process of switching between the light-transmitting state and the light-blocking state of the shutter will be described.

As illustrated in FIG. 2B, each shutter includes an incident-side polarizer and an emitting-side polarizer, and further includes a liquid crystal layer between the incident-side polarizer and the emitting-side polarizer. Moreover, the incident-side polarizer and the emitting-side polarizer are orthogonal to each other as illustrated in FIG. 2B. Here, as illustrated in FIG. 2B, in an "OFF" state where no voltage is applied, light having passed through the incident-side polarizer passes through the emitting-side polarizer with the polarization axis rotated by 90 degrees due to the effect of the liquid crystal layer. That is, a shutter in which no voltage is applied enters the light-transmitting state.

On the other hand, as illustrated in FIG. 2B, in an "ON" state where a voltage is applied, since the polarization rotating effect due to liquid crystal molecules of the liquid crystal layer disappears, light having passed through the incident-side polarizer is blocked by the emitting-side polarizer. That is, a shutter in which a voltage is applied enters the light-blocking state.

Thus, for example, the infrared emitting unit emits infrared light in a period where a left-eye image is displayed on the monitor. Moreover, the infrared receiving unit applies a voltage to the right-eye shutter without applying a voltage to the left-eye shutter in a period where infrared light is received. In this way, as illustrated in FIG. 2A, since the right-eye shutter enters the light-blocking state and the left-eye shutter enters the light-transmitting state, a left-eye image enters the left eye of the viewer. On the other hand, the infrared emitting unit stops emitting infrared light in a period where a right-eye image is displayed on the monitor. Moreover, the infrared receiving unit applies a voltage to the left-eye shutter without applying a voltage to the right-eye shutter in a period where no infrared light is received. In this way, since the left-eye shutter enters the light-blocking state and the right-eye shutter enters the light-transmitting state, a right-eye image enters the right eye of the viewer. As above, the stereoscopic display monitor illustrated in FIGS. 2A and 2B displays images which can be perceived stereoscopically by the viewer by switching the images displayed on the monitor and the shutter states in association. Another example of the stereoscopic display monitor which can display 2-parallax images stereoscopically is known, such as a monitor which employs polarized glasses method in addition to the monitor which employs shutter method.

Furthermore, another example of stereoscopic display monitors that are commercialized in recent years is known, such as a stereoscopic display monitor which enables multi-parallax images such as 9-parallax images to be perceived stereoscopically with the naked eyes of a viewer by using a beam controller such as a lenticular lens. The stereoscopic display monitor enables stereoscopic display with a binocular parallax and also enables a video viewed with movement of the viewpoint of a viewer to be perceived stereoscopically with a varying movement parallax.

Figure 3:
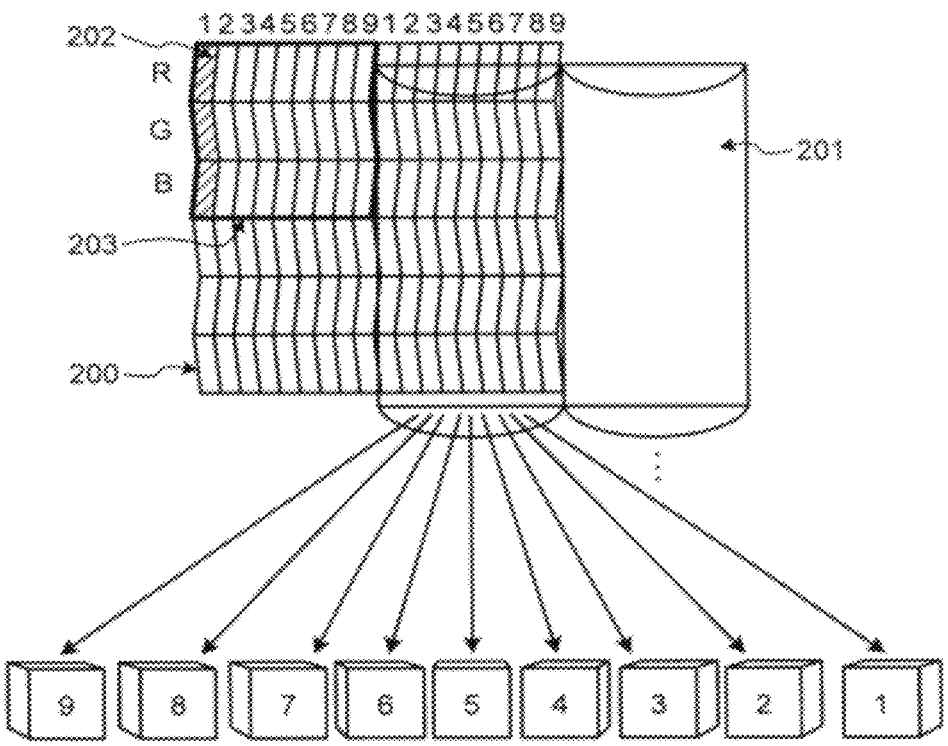
FIG. 3 is a diagram for describing an example of a stereoscopic display monitor that performs stereoscopic display using 9-parallax images.

FIG. 3 is a diagram for describing an example of a stereoscopic display monitor that performs stereoscopic display using 9-parallax images. In the stereoscopic display monitor illustrated in FIG. 3, a beam controller is disposed on the front surface of a planar display surface 200 such as a liquid crystal panel. For example, in the stereoscopic display monitor illustrated in FIG. 3, a vertical lenticular sheet 201 of which the optical aperture extends in the vertical direction is attached to the front surface of the display surface 200 as the beam controller. In the example illustrated in FIG. 3, although the vertical lenticular sheet 201 is attached so that the convex portion thereof is on the front surface, the vertical lenticular sheet 201 may be attached so that the convex portion faces the display surface 200.

As illustrated in FIG. 3, pixels 202 of which the aspect ratio is 3:1, and in which three sub pixels of the colors red (R), green (G), and blue (B) are arranged in the vertical direction are arranged on the display surface 200 in a matrix form. The stereoscopic display monitor illustrated in FIG. 3 converts 9-parallax images made up of nine images into intermediate images arranged in a predetermined format (for example, a grid form) and outputs the intermediate images to the display surface 200. That is, the stereoscopic display monitor illustrated in FIG. 3 outputs 9-parallax images by allocating the respective nine pixels located at the same positions as the 9-parallax images to nine columns of pixels 202. The nine columns of pixels 202 serve as unit pixels 203 that display nine images having different viewpoint positions simultaneously.

The 9-parallax images output simultaneously to the display surface 200 as the unit pixels 203 are radiated, for example, by an LED (light emitting diode) backlight as parallel light and are further radiated by the vertical lenticular sheet 201 in multiple directions. Since the light of the respective pixels of the 9-parallax image is radiated in multiple directions, the light entering the right and left eyes of a viewer changes in association with the position (the position of a viewpoint) of the viewer. That is, depending on the viewing angle of the viewer, the parallax image entering the right eye and the parallax image entering the left eye have different parallax angles. In this way, the viewer can perceive a subject stereoscopically at each of the nine positions illustrated in FIG. 3, for example. Moreover, the viewer can perceive the subject stereoscopically in a state of opposing in front of the subject at the position "5" illustrated in FIG. 3 and can perceive the subject stereoscopically in a state of changing the orientation of the subject at the respective positions other than the position "5" illustrated in FIG. 3. The stereoscopic display monitor illustrated in FIG. 3 is an example only. The stereoscopic display monitor that displays 9-parallax images may use a liquid crystal panel with a horizontal stripe pattern of "RRR . . . , GGG . . . , BBB . . . " as illustrated in FIG. 3, and may use a liquid crystal panel with a vertical stripe pattern of "RGBRGB . . . ." Moreover, the stereoscopic display monitor illustrated in FIG. 3 may use a vertical lens method in which the lenticular sheet is vertically arranged as illustrated in FIG. 3, and may use an oblique lens method in which the lenticular sheet is obliquely arranged.

Hereinabove, a configuration example of the image processing system 1 according to the first embodiment has been described briefly. The application of the image processing system 1 is not limited to the case where the PACS is incorporated therein. For example, the image processing system 1 is similarly applied to a case where an electronic chart system that manages an electronic chart to which medical images are attached is incorporated. In this case, the image archiving device 120 is a database that archives electronic charts. Moreover, for example, the image processing system 1 is similarly applied to a case where an HIS (hospital information system) or an RIS (radiology information system) is incorporated. Moreover, the image processing system 1 is not limited to the configuration example described above. The functions possessed by the respective apparatuses and the allotment thereof may be appropriately changed depending on the form of application.

Figure 4:
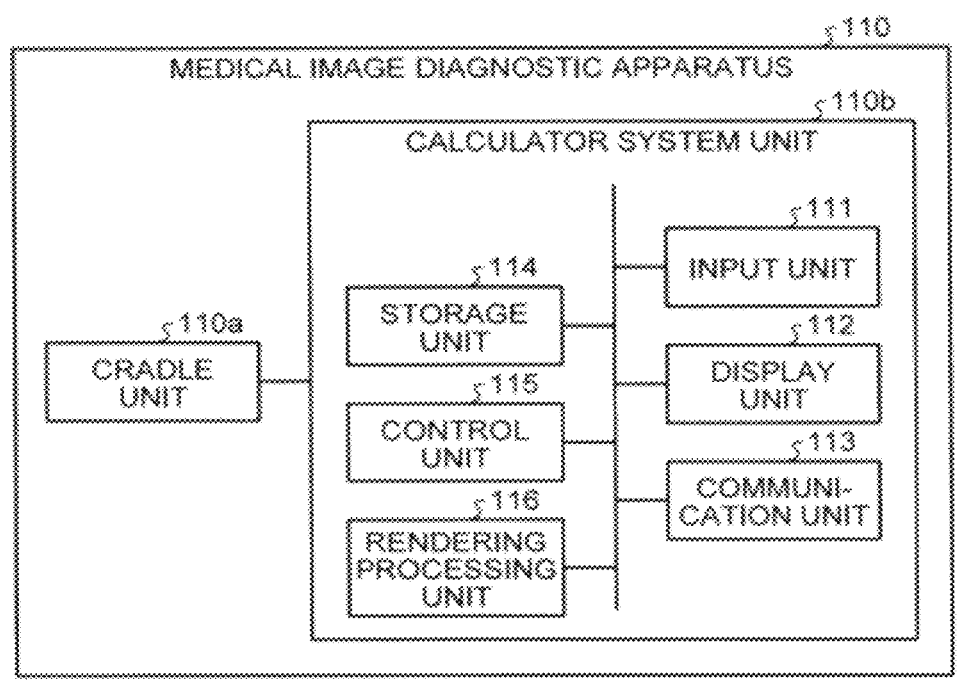
FIG. 4 is a diagram for describing a configuration example of a medical image diagnostic apparatus according to the first embodiment.

Next, a configuration example of the medical image diagnostic apparatus 110 according to the first embodiment will be described with reference to FIG. 4. FIG. 4 is a diagram for describing a configuration example of the medical image diagnostic apparatus 110 according to the first embodiment.

As illustrated in FIG. 4, the medical image diagnostic apparatus 110 according to the first embodiment includes a cradle unit 110a and a calculator system unit 110b. The cradle unit 110a includes respective units used for imaging, and for example, when the medical image diagnostic apparatus 110 is an X-ray CT apparatus, the cradle unit 110a includes an X-ray tube, detectors, a rotating arm, a bed, and the like. On the other hand, the calculator system unit 110b includes an input unit 111, a display unit 112, a communication unit 113, a storage unit 114, a control unit 115, and a rendering processing unit 116.

The input unit 111 is a mouse, a keyboard, a trackball, or the like, and receives the input of various operations on the medical image diagnostic apparatus 110 from an operator. Specifically, the input unit 111 according to the first embodiment receives the input of imaging plans, the input of imaging instructions, the input of conditions regarding rendering processes (hereinafter referred to as rendering conditions), and the like.

The display unit 112 is a liquid crystal panel or the like serving as the stereoscopic display monitor and displays various types of information. Specifically, the display unit 112 according to the first embodiment displays a GUI (graphical user interface) for receiving various operations from an operator, a group of parallax images as display images, and the like. The communication unit 113 is an NIC (network interface card) or the like and performs communication with other apparatuses.

The storage unit 114 is a hard disk, a semiconductor memory device, or the like, and stores various types of information. Specifically, the storage unit 114 according to the first embodiment stores imaging data collected by imaging. Moreover, the storage unit 114 according to the first embodiment stores volume data generated from the imaging data, volume data under rendering processes, the group of parallax images generated by the rendering processes, and the like.

The control unit 115 is an electronic circuit such as a CPU (central processing unit) or an MPU (micro processing unit), or an integrated circuit such as an ASIC (application specific integrated circuit) or an FPGA (field programmable gate array), and performs control of the entire medical image diagnostic apparatus 110.

For example, the control unit 115 according to the first embodiment controls the display of GUI and the display of the group of parallax images on the display unit 112. Moreover, for example, the control unit 115 controls the imaging performed by controlling the respective units included in the cradle unit 110a and transmission/reception of volume data or parallax images to/from the image archiving device 120, performed via the communication unit 113. Moreover, for example, the control unit 115 controls the rendering processes by the rendering processing unit 116. Moreover, for example, the control unit 115 controls the reading of various types of data from the storage unit 114 and the storing of the data in the storage unit 114.

The rendering processing unit 116 performs various rendering processes on the volume data read from the storage unit 114 under the control of the control unit 115 to generate a group of parallax images. Specifically, first, the rendering processing unit 116 according to the first embodiment reads volume data from the storage unit 114 and performs preprocessing on the volume data. Subsequently, the rendering processing unit 116 performs a volume rendering process on the preprocessed volume data to generate a group of parallax images. Subsequently, the rendering processing unit 116 generates 2-dimensional images in which various types of information (scale, patient names, examination items, and the like) are drawn and superimposes the generated 2-dimensional images on each of the group of parallax images to thereby generate 2-dimensional output images. Moreover, the rendering processing unit 116 stores the generated group of parallax images and the 2-dimensional output images in the storage unit 114. In the first embodiment, the rendering process is the entire image processing performed on the volume data, and the volume rendering process is a process of generating 2-dimensional images including 3-dimensional information within the rendering process.

Figure 5:
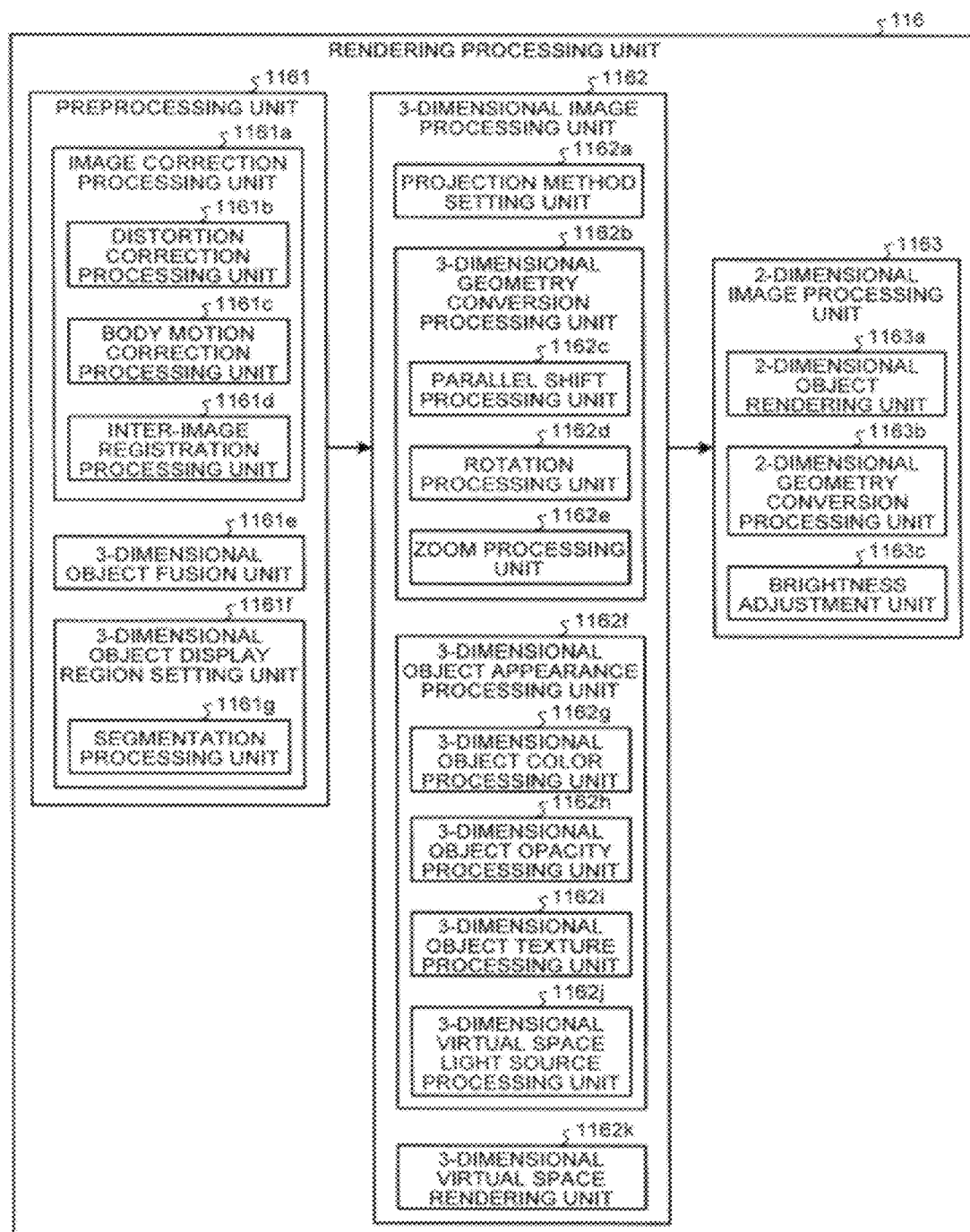
FIG. 5 is a diagram for describing a configuration example of a rendering processing unit illustrated in FIG. 4.

FIG. 5 is a diagram for describing a configuration example of the rendering processing unit illustrated in FIG. 4. As illustrated in FIG. 5, the rendering processing unit 116 includes a preprocessing unit 1161, a 3-dimensional image processing unit 1162, and a 2-dimensional image processing unit 1163. The preprocessing unit 1161 performs preprocessing on volume data, the 3-dimensional image processing unit 1162 generates a group of parallax images from the preprocessed volume data, and the 2-dimensional image processing unit 1163 generates 2-dimensional output images in which various types of information are superimposed on the group of parallax images. Hereinafter, the respective units will be described in order.

The preprocessing unit 1161 is a processing unit that performs various types of preprocessing when performing rendering processes on volume data. The preprocessing unit 1161 includes an image correction processing unit 1161*a*, a 3-dimensional object fusion unit 1161*e*, and a 3-dimensional object display region setting unit 1161*f*.

The image correction processing unit 1161*a* is a processing unit that performs an image correction process when processing two sets of volume data as one set of volume data. As illustrated in FIG. 5, the image correction processing unit 1161*a* includes a distortion correction processing unit 1161*b*, a body motion correction processing unit 1161*c*, and an inter-image registration processing unit 1161*d*. For example, the image correction processing unit 1161*a* performs an image correction process when processing the volume data of PET images and the volume data of X-ray CT images generated by a PET-CT apparatus as one set of volume data. Alternatively, the image correction processing unit 1161*a* performs an image correction process when processing the volume data of T1-enhanced images and the volume data of T2-enhanced images generated by an MRI apparatus as one set of volume data.

Moreover, the distortion correction processing unit 1161*b* corrects a data distortion in individual sets of volume data, resulting from the collecting conditions when collecting data using the medical image diagnostic apparatus 110. Moreover, the body motion correction processing unit 1161*c* corrects a movement resulting from a body motion of a subject when collecting data used for generating the individual sets of volume data. Moreover, the inter-image registration processing unit 1161*d* performs registration between two sets of volume data which have been corrected by the distortion correction processing unit 1161*b* and the body motion correction processing unit 1161*c*, using a cross-correlation method or the like, for example.

The 3-dimensional object fusion unit 1161*e* fuses multiple sets of volume data which have been registered by the inter-image registration processing unit 1161*d*. The processes of the image correction processing unit 1161*a* and the 3-dimensional object fusion unit 1161*e* are not performed when the rendering process is performed with respect to a single set of volume data.

The 3-dimensional object display region setting unit 1161*f* is a processing unit that sets a display region corresponding to a display target organ designated by an operator. The 3-dimensional object display region setting unit 1161*f* includes a segmentation processing unit 1161*g*. The segmentation processing unit 1161*g* is a processing unit that extracts an organ such as the heart, the lung, or blood vessels, designated by an operator using a region growing method based on the pixel values (voxel values) of volume data, for example.

The segmentation processing unit 1161*g* does not perform a segmentation process when a display target organ is not designated by the operator. Moreover, when multiple display target organs are designated by the operator, the segmentation processing unit 1161*g* extracts the corresponding multiple organs. Moreover, the processing of the segmentation processing unit 1161*g* may be executed over and over in response to a fine adjustment request from an operator who referred to a rendering image.

The 3-dimensional image processing unit 1162 performs a volume rendering process on the volume data preprocessed by the preprocessing unit 1161. As processing units that perform the volume rendering process, the 3-dimensional image processing unit 1162 includes a projection method setting unit 1162*a*, a 3-dimensional geometry conversion processing unit 1162*b*, a 3-dimensional object appearance processing unit 1162*f*, and a 3-dimensional virtual space rendering unit 1162*k*.

The projection method setting unit 1162*a* determines a projection method for generating a group of parallax images. For example, the projection method setting unit 1162*a* determines whether the volume rendering process is to be executed by a parallel projection method or a perspective projection method.

The 3-dimensional geometry conversion processing unit 1162*b* is a processing unit that determines information for geometrically converting the volume data to be subjected to the volume rendering process into a 3-dimensional space. The 3-dimensional geometry conversion processing unit 1162*b* includes a parallel shift processing unit 1162*c*, a rotation processing unit 1162*d*, and a zoom processing unit 1162*e*. The parallel shift processing unit 1162*c* is a processing unit that determines the amount of parallel shift of volume data when the viewpoint position is shifted in parallel during the volume rendering process. The rotation processing unit 1162*d* is a processing unit that determines the amount of rotational movement of volume data when the viewpoint position is rotated during the volume rendering process. Moreover, the zoom processing unit 1162*e* is a processing unit that determines the zoom ratio of volume data when it is requested to zoom in or out the group of parallax images.

The 3-dimensional object appearance processing unit 1162*f* includes a 3-dimensional object color processing unit 1162*g*, a 3-dimensional object opacity processing unit 1162*h*, a 3-dimensional object texture processing unit 1162*i*, and a 3-dimensional virtual space light source processing unit 1162*j*. The 3-dimensional object appearance processing unit 1162*f* performs a process of determining the display state of the group of parallax images displayed in accordance with the request of the operator, for example, using these processing units.

The 3-dimensional object color processing unit 1162*g* is a processing unit that determines the colors to be filled in the respective segmented regions of the volume data. The 3-dimensional object opacity processing unit 1162*h* is a processing unit that determines the opacity of respective voxels constituting each of the segmented regions of the volume data. Regions of the volume data behind a region having opacity of "100%" are not drawn in the group of parallax images. Moreover, regions of the volume data having opacity of "0%" are not drawn in the group of parallax images.

The 3-dimensional object texture processing unit 1162*i* is a processing unit that determines the material of respective segmented regions of the volume data to thereby adjust the texture when the regions are drawn. The 3-dimensional virtual space light source processing unit 1162*j* is a processing unit that determines the position of a virtual light source disposed in a 3-dimensional virtual space and the type of the virtual light source when performing the volume rendering process on the volume data. Examples of the type of the virtual light source include a light source that emits parallel light beams from the infinity and a light source that emits radiating light beams from a viewpoint.

The 3-dimensional virtual space rendering unit 1162*k* performs the volume rendering process to the volume data to thereby generate a group of parallax images. Moreover, when performing the volume rendering process, the 3-dimensional virtual space rendering unit 1162*k* uses various types of information determined by the projection method setting unit 1162*a*, the 3-dimensional geometry conversion processing unit 1162*b*, and the 3-dimensional object appearance processing unit 1162*f* as necessary.

Here, the volume rendering process by the 3-dimensional virtual space rendering unit 1162*k* is performed in accordance with the rendering condition. For example, the rendering condition is "parallel projection method" or "perspective projection method." Moreover, for example, the rendering condition is "reference viewpoint position and parallax angle." Moreover, for example, the rendering condition is "parallel shift of viewpoint position," "rotational movement of viewpoint position," "zoom-in of group of parallax images," and "zoom-out of group of parallax images." Moreover, for example, the rendering condition is "filling color," "transparency," "texture," "position of virtual light source," and "type of virtual light source." These rendering conditions may be received from the operator via the input unit 111 and may be set as initial settings. In any cases, the 3-dimensional virtual space rendering unit 1162*k* receives the rendering conditions from the control unit 115 and performs the volume rendering process on the volume data in accordance with the rendering conditions. Moreover, in this case, since the projection method setting unit 1162*a*, the 3-dimensional geometry conversion processing unit 1162*b*, and the 3-dimensional object appearance processing unit 1162*f* determine various types of necessary information in accordance with the rendering conditions, the 3-dimensional virtual space rendering unit 1162*k* generates a group of parallax images using these various types of determined information.

Figure 6:
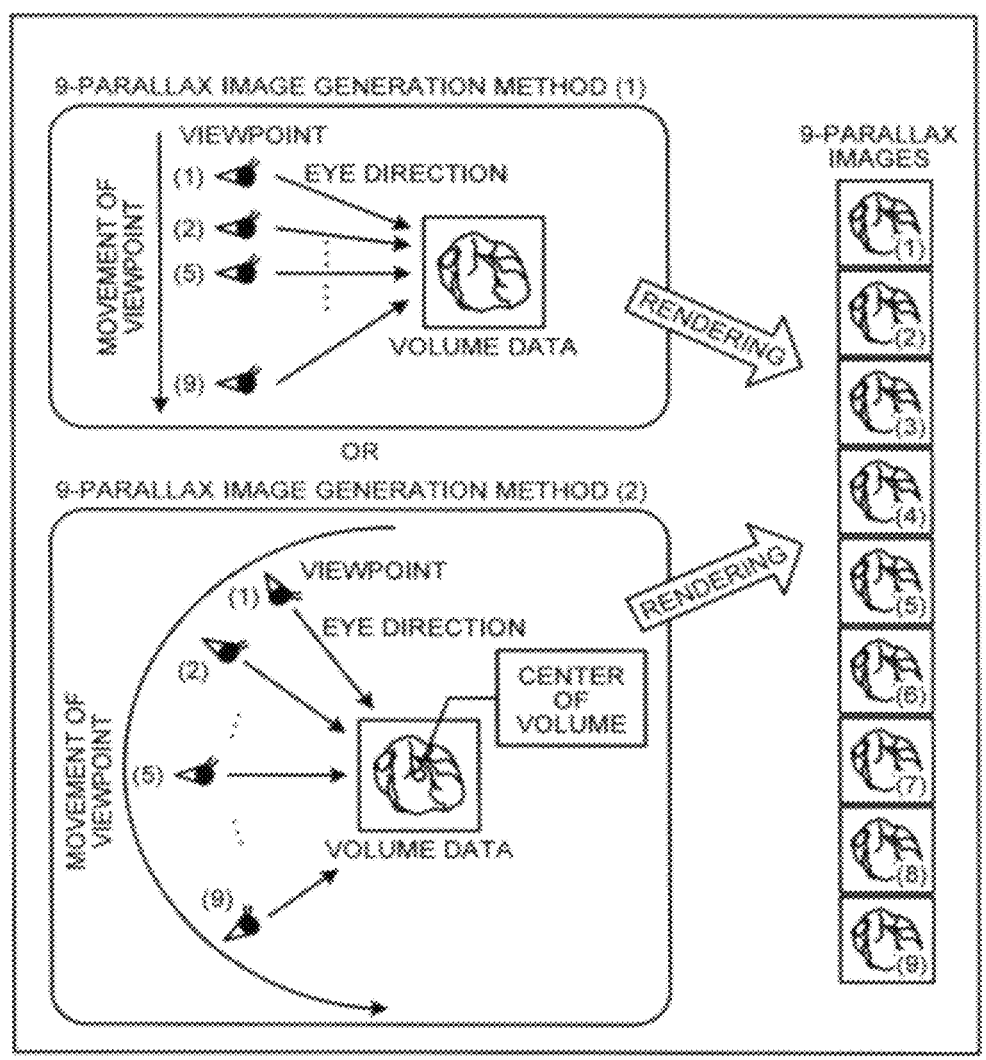
FIG. 6 is a diagram for describing an example of a volume rendering process according to the first embodiment.

FIG. 6 is a diagram for describing an example of the volume rendering process according to the first embodiment. For example, as illustrated in "9-parallax image generation method (1)" of FIG. 6, it is assumed that the 3-dimensional virtual space rendering unit 1162*k* receives a parallel projection method as the rendering condition and receives a reference viewpoint position of (5) and a parallax angle of "1 degree." In this case, the 3-dimensional virtual space rendering unit 1162*k* shifts the viewpoint positions in parallel to the positions of (1) to (9) so that the parallax angle is "1 degree" to thereby generate nine parallax images by the parallel projection method so that the difference between parallax angles (the angle between the eye directions) is 1 degree. When performing the parallel projection method, the 3-dimensional virtual space rendering unit 1162*k* sets a light source that emits parallel light beams from the infinity along the eye direction.

Alternatively, as illustrated in "9-parallax image generation method (2)" of FIG. 6, it is assumed that the 3-dimensional virtual space rendering unit 1162*k* receives a perspective projection method as the rendering condition and receives a reference viewpoint position of (5) and a parallax angle of "1 degree." In this case, the 3-dimensional virtual space rendering unit 1162*k* rotates the viewpoint position about the center (weighted center) of the volume data to the positions of (1) to (9) so that the parallax angle is "1 degree" to thereby generate nine parallax images by the perspective projection method so that the difference between parallax angles is 1 degree. When performing the perspective projection method, the 3-dimensional virtual space rendering unit 1162*k* sets a point light source or a field light source that emits light 3-dimensionally in a radial form about the eye direction at respective viewpoints. Moreover, when performing the perspective projection method, the viewpoints (1) to (9) may be shifted in parallel depending on the rendering condition.

The 3-dimensional virtual space rendering unit 1162*k* may perform the volume rendering process using both the parallel projection method and the perspective projection method by setting a light source that emits light 2-dimensionally in a radial form about the eye direction with respect to the vertical direction of volume rendering images to be displayed and emits parallel light beams from the infinity along the eye direction with respect to the horizontal direction of the volume rendering images to be displayed.

The nine parallax images generated in this way are the group of parallax images. In the first embodiment, the nine parallax images are converted into intermediate images arranged in a predetermined format (for example, a grid form) by the control unit 115, for example, and are output to the display unit 112 as the stereoscopic display monitor. Then, the operator of the workstation 130 can perform operations for generating the group of parallax images while checking the stereoscopic medical images displayed on the stereoscopic display monitor.

In the example of FIG. 6, although a case where a projection method, a reference viewpoint position, and a parallax angle are received as the rendering conditions has been described, even when other conditions are received as the rendering conditions, the 3-dimensional virtual space rendering unit 1162*k* generates a group of parallax images while reflecting the respective rendering conditions in the same manner.

Moreover, the 3-dimensional virtual space rendering unit 1162*k* also has a function of performing an MPR (multi-planar reconstruction) method as well as the volume rendering method to reconstruct MPR images from volume data. The 3-dimensional virtual space rendering unit 1162*k* has a function of performing "curved MPR" and a function of performing "intensity projection."

Subsequently, the group of parallax images generated from the volume data by the 3-dimensional image processing unit 1162 is set as an underlay. Moreover, an overlay in which various types of information (scale, patient names, examination items, and the like) are drawn is superimposed on the underlay, and the resulting images are set as 2-dimensional output images. The 2-dimensional image processing unit 1163 is a processing unit that generates 2-dimensional output images by performing image processing on the overlay and the underlay. As illustrated in FIG. 5, the 2-dimensional image processing unit 1163 includes a 2-dimensional object rendering unit 1163*a*, a 2-dimensional geometry conversion processing unit 1163*b*, and a brightness adjustment unit 1163*c*. For example, the 2-dimensional image processing unit 1163 generates nine 2-dimensional output images by superimposing one overlay to each of nine parallax images (underlays) in order to decrease the load necessary for the process of generating 2-dimensional output images.

The 2-dimensional object rendering unit 1163*a* is a processing unit that renders various types of information to be drawn on the overlay. The 2-dimensional geometry conversion processing unit 1163*b* is a processing unit that performs the process of shifting in parallel or rotationally moving the positions of various types of information drawn on the overlay and the process of zooming in or out various types of information drawn on the overlay.

Moreover, the brightness adjustment unit 1163*c* is a processing unit that performs a brightness conversion process, and for example, is a processing unit that adjusts the brightness of the overlay and the underlay in accordance with image processing parameters such as gradation of a stereoscopic display monitor at the output destination, a WW (window width), or a WL (window level).

The 2-dimensional output images generated in this way are stored in the storage unit 114 by the control unit 115, for example, and are then transmitted to the image archiving device 120 via the communication unit 113. For example, when the workstation 130 or the terminal device 140 acquires the 2-dimensional output images from the image archiving device 120 and displays the same on the stereoscopic display monitor after converting into intermediate images arranged in a predetermined format (for example, a grid form), doctors or examiners who are viewers can view stereoscopic medical images in which various types of information (scale, patient names, examination items, and the like) are drawn.

Meanwhile, as described above, the medical image diagnostic apparatus 110 according to the first embodiment also displays icons displayed on the operation screen so as to be perceived stereoscopically. Moreover, the icons displayed stereoscopically in the first embodiment are icons (hereinafter, thumbnail icons) for allowing operators to select medical image data.

From the past, the medical image diagnostic apparatus 110 has displayed thumbnail icons on the operation screen in order to allow operators to select medical image data. For example, thumbnail icons which are designs for reduced medical images or thumbnail icons which are designs for artificial medical images have been displayed. However, the medical image data stored in the medical image diagnostic apparatus 110 includes various types of data including volume data, 2-dimensional images after rendering processes, a group of parallax images, and a group of 2-dimensional output images in which various types of information are superimposed on each of the group of parallax images. Thus, when only the thumbnail icons of reduced medical images or artificial medical images are just displayed on the operation screen, it was difficult for the operators to understand the type of medical image data.

In this regard, the medical image diagnostic apparatus 110 according to the first embodiment determines whether thumbnail icons will be displayed as images (hereinafter referred to as stereoscopic images) which can be perceived stereoscopically or as the other images (hereinafter referred to as planar images) depending on the content of the medical image data selected by the operator. Moreover, when thumbnail icons are displayed as stereoscopic images, the medical image diagnostic apparatus 110 according to the first embodiment displays thumbnail icons so that the stereoscopic effect of the thumbnail icon reflects the quantity of medical image data (for example, an imaging range in the body axis direction included in the medical image data, and the number of medical image data included in volume data when the medical image data is volume data). As a result, the operation screen is displayed appropriately, and the operator can understand the type of image and the quantity of medical image data just by watching thumbnail icons. This will be described in detail below.

Figure 7:
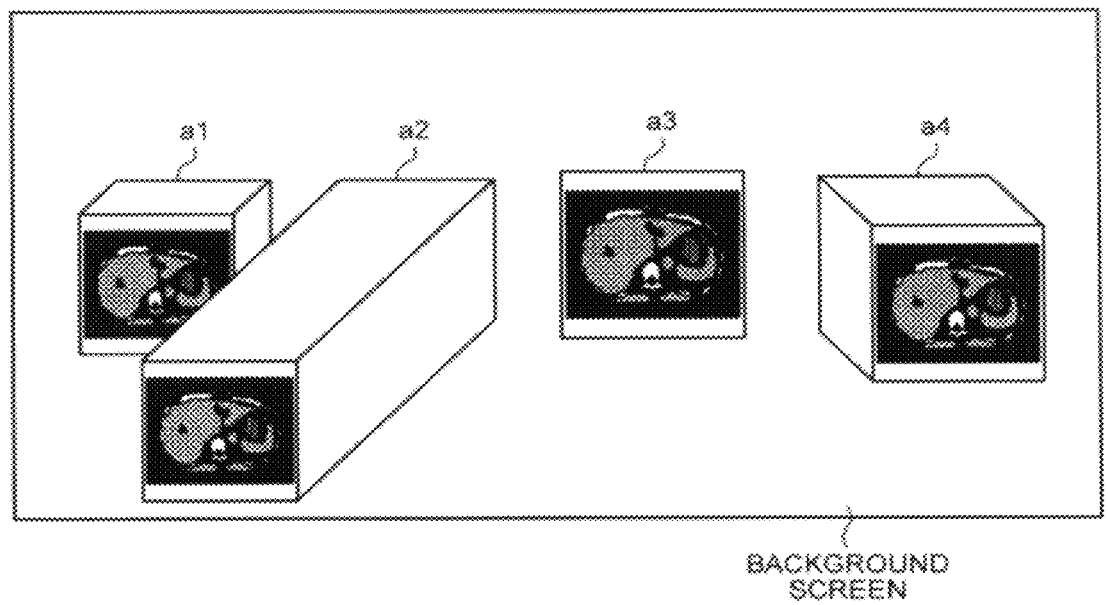
FIG. 7 is a diagram for describing a display method according to the first embodiment.
Figure 8:
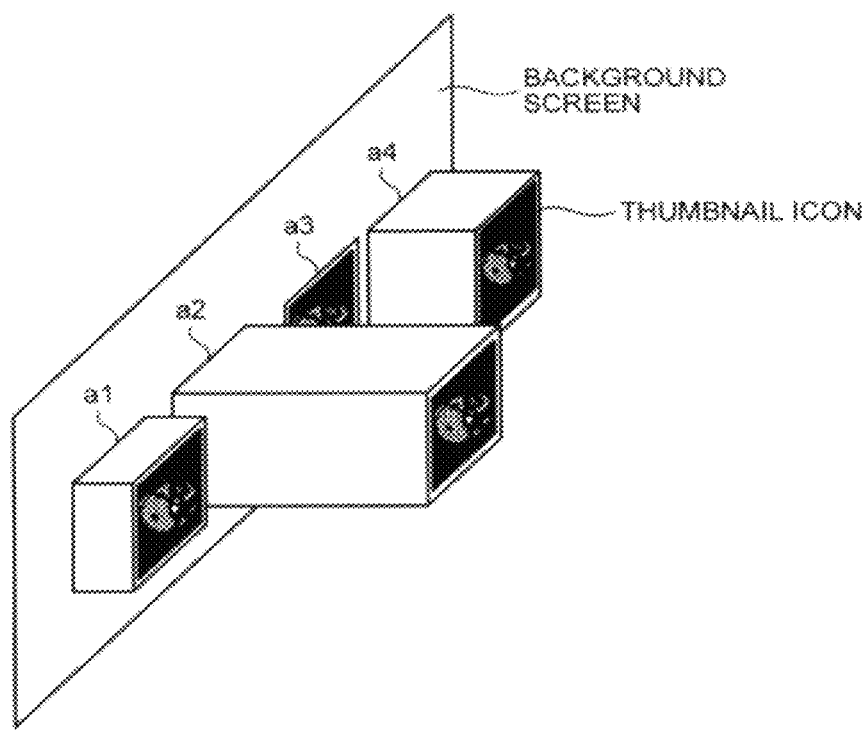
FIG. 8 is a diagram for describing a display method according to the first embodiment.

FIGS. 7 and 8 are diagrams for describing a display example according to the first embodiment. In FIGS. 7 and 8, a region (hereinafter referred to as a thumbnail region) for displaying thumbnail icons, extracted from the operation screen is illustrated for the sake of convenience. As illustrated in FIG. 7, although the medical image diagnostic apparatus 110 displays multiple thumbnail icons to be aligned, thumbnail icons a1, a2, and a4 are displayed as stereoscopic images, and a thumbnail icon a3 is displayed as a planar image. Moreover, as illustrated in FIG. 8, the medical image diagnostic apparatus 110 displays the thumbnail icons so that the thumbnail icon a4 has a greater stereoscopic effect than a1, and the thumbnail icon a2 has a greater stereoscopic effect than a4.

Although the stereoscopic effect in the first embodiment means the sense of frontward protrusion from a reference surface (the background screen in FIGS. 7 and 8) of the operation screen, the embodiments are not limited to this, but the stereoscopic effect may be the sense of depth in the depth direction from the reference surface or a combination of the sense of protrusion and the sense of depth.

Figure 9:
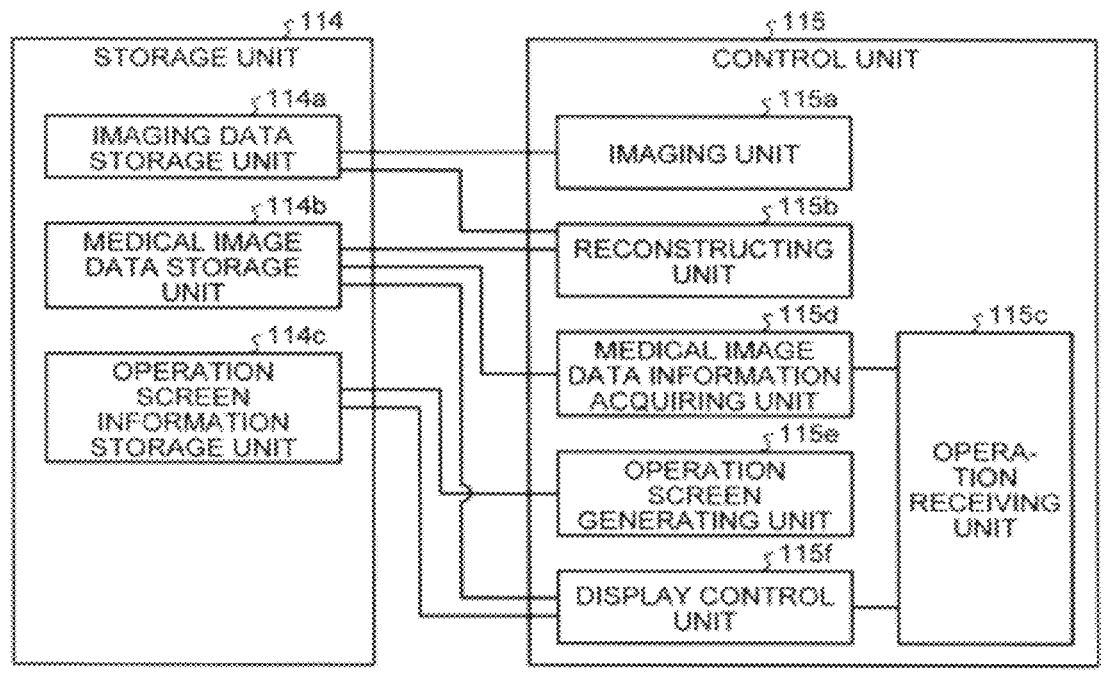
FIG. 9 is a diagram for describing a configuration example of a storage unit and a control unit according to the first embodiment.

FIG. 9 is a diagram for describing a configuration example of the storage unit 114 and the control unit 115 according to the first embodiment. As illustrated in FIG. 9, the storage unit 114 of the medical image diagnostic apparatus 110 according to the first embodiment includes an imaging data storage unit 114*a*, a medical image data storage unit 114*b*, and an operation screen information storage unit 114*c*.

The imaging data storage unit 114*a* stores imaging data in accordance with the operation of an imaging unit 115*a* described later. Moreover, the imaging data stored by the imaging data storage unit 114*a* is used for the processing by a reconstructing unit 115*b* described later.

The medical image data storage unit 114*b* stores volume data, 2-dimensional images after rendering processes, a group of parallax images, a group of 2-dimensional output images in which various types of information are superimposed on each of the group of parallax images, and the like in accordance with the operation of the reconstructing unit 115*b* described later. The medical image data stored by the medical image data storage unit 114*b* is used for the processing by a medical image data information acquiring unit 115*d* and a display control unit 115*f* described later.

The operation screen information storage unit 114*c* stores basic information for displaying the operation screen, which is stored in advance, for example, when the medical image diagnostic apparatus 110 is set up, and stores operation screen display information in which thumbnail icons or the like are added to basic information in accordance with the operation of an operation screen generating unit 115*e* described later. Moreover, the basic information stored by the operation screen information storage unit 114*c* is used for the processing by the operation screen generating unit 115*e*, and the operation screen display information stored by the operation screen information storage unit 114*c* is used for the processing by the display control unit 115*f*.

Next, as illustrated in FIG. 9, the control unit 115 of the medical image diagnostic apparatus 110 according to the first embodiment includes the imaging unit 115*a*, the reconstructing unit 115*b*, an operation receiving unit 115*c*, the medical image data information acquiring unit 115*d*, the operation screen generating unit 115*e*, and the display control unit 115*f*.

The imaging unit 115*a* performs imaging by controlling the respective units of the cradle unit 110*a* in accordance with predetermined imaging conditions. Moreover, the imaging unit 115*a* stores the imaging data collected by imaging in the imaging data storage unit 114*a*. For example, when the medical image diagnostic apparatus 110 is an X-ray CT apparatus, the imaging unit 115*a* collects projection data by controlling an X-ray tube, detectors, a rotating arm, and the like in accordance with predetermined imaging conditions and stores the collected projection data in the imaging data storage unit 114*a*.

The reconstructing unit 115*b* reads imaging data from the imaging data storage unit 114*a* and performs a reconstructing process on the read imaging data to thereby generate volume data. Moreover, the reconstructing unit 115*b* performs a rendering process on the generated volume data in cooperation with the rendering processing unit 116 to thereby generate 2-dimensional images after the rendering process, a group of parallax images, a group of 2-dimensional output images in which various types of information are superimposed on each of the group of parallax images, and the like. Moreover, the reconstructing unit 115*b* stores the generated volume data, 2-dimensional images after the rendering process, group of parallax images, group of 2-dimensional output images, and the like in the medical image data storage unit 114*b*.

The operation receiving unit 115*c* receives operations via the input unit 111. For example, the operation receiving unit 115*c* receives an operation for an operation screen display instruction. In this case, the operation receiving unit 115*c* notifies the medical image data information acquiring unit 115*d* of the note of the reception of the operation screen display instruction together with a patient ID and an examination ID input at an imaging planning step, for example. Moreover, for example, the operation receiving unit 115*c* receives an operation of selecting a thumbnail icon displayed on the operation screen. In this case, the operation receiving unit 115*c* notifies the display control unit 115*f* of the selected thumbnail icon.

The medical image data information acquiring unit 115*d* acquires medical image data information necessary for generating a thumbnail region displayed on the operation screen. Specifically, upon receiving the notification of the reception of the operation for the operation screen display instruction from the operation receiving unit 115*c*, the medical image data information acquiring unit 115*d* specifies the corresponding medical image data by referring to the medical image data storage unit 114*b* using a patient ID and an examination ID, for example. Subsequently, the medical image data information acquiring unit 115*d* acquires the type of medical image data, an imaging range in the body axis direction included in the medical image data, and the number of medical image data included in volume data when the medical image data is volume data, for example, as the medical image data information of the specified medical image data. Moreover, the medical image data information acquiring unit 115*d* notifies the operation screen generating unit 115*e* of the acquired medical image data information. The medical image data information is one which is stored in the medical image data storage unit 114*b*, and in which the information input at an imaging planning step, for example, is stored together with imaging data, volume data generated later, and the like.

The operation screen generating unit 115*e* generates operation screen display information. Specifically, upon receiving the notification of medical image data information from the medical image data information acquiring unit 115*d*, the operation screen generating unit 115*e* acquires basic information for displaying the operation screen by referring to the operation screen information storage unit 114*c* and generates a thumbnail region based on the medical image data information to thereby generate operation screen display information in which thumbnail icons or the like are added to the basic information. Moreover, the operation screen generating unit 115*e* stores the generated operation screen display information in the operation screen information storage unit 114*c* and notifies the display control unit 115*f* of the note indicating that the operation screen display information has been generated.

Generation of the thumbnail region by the operation screen generating unit 115*e* will be described in detail. FIGS. 10 and 11 are diagrams for describing generation of the thumbnail region according to the first embodiment. For example, the operation screen generating unit 115*e* stores a table (see FIGS. 10 and 11) for generating thumbnail icons, and a group of parallax images for thumbnail icons and rectangular planar images for thumbnail icons generated in advance by performing computation processing so that a cuboid can be perceived stereoscopically. Moreover, the operation screen generating unit 115*e* stores multiple patterns of groups of parallax images of which the heights of cuboids (frontward heights from the reference surface of the operation screen) are different so that the stereoscopic effect of thumbnail icons reflects the quantity of medical image data. For example, the multiple patterns of groups of parallax images are multiple patterns of groups of parallax images having different parallax angles, and generally, the stereoscopic effect increases as the parallax angle increases.

As illustrated in FIG. 10, the operation screen generating unit 115*e* stores the correspondence between an imaging range and a thumbnail icon image as the table for generating thumbnail icons. For example, the operation screen generating unit 115*e* stores a thumbnail icon image "head.jpeg" in correlation with an imaging range "head." The thumbnail icon image is one image or a representative image included in medical image data, for example. For example, when medical image data of 500 axial planes are included in the medical image data, the thumbnail icon image is medical image data of the first axial plane or medical image data of the 250th axial plane corresponding to the center of the imaging range. Alternatively, the thumbnail icon image may be an MPR image generated from the medical image data.

Alternatively, the thumbnail icon image may be medical image data collected at the time of scanogram scanning.

Moreover, as illustrated in FIG. 11, the operation screen generating unit 115e stores the correspondence between the number of medical image data and a stereoscopic effect as the table for generating thumbnail icons. For example, the operation screen generating unit 115e stores a stereoscopic effect "2" in correlation with the number "upto 200 (from 101 to 200)." The example illustrated in FIG. 11 represents that the stereoscopic effect increases as the number assigned to the stereoscopic effect increases. Moreover, in the first embodiment, although the stereoscopic effect is reflected based on the number of medical image data, the embodiments are not limited to this, but the stereoscopic effect may be reflected based on the imaging range. For example, the stereoscopic effect of the imaging range "whole body" may be greater than the stereoscopic effect of the imaging range "head."

Meanwhile, as described above, the operation screen generating unit 115e according to the first embodiment receives the type of medical image data, the imaging range in the body axis direction included in the medical image data, and the number of medical image data included in volume data when the medical image data is volume data, as the medical image data information.

For example, the operation screen generating unit 115e receives the type of medical image data "volume data," the imaging range in body axis direction "head," and the number of medical image data "200" as first medical image data information. Moreover, the operation screen generating unit 115e receives the type of medical image data "MPR image," the imaging range in body axis direction "head," and the number of medical image data "1" as second medical image data information. Moreover, the operation screen generating unit 115e receives the type of medical image data "volume data," the imaging range in body axis direction "abdomen," and the number of medical image data "500" as third medical image data information. Moreover, the operation screen generating unit 115e receives the type of medical image data "MPR image," the imaging range in body axis direction "abdomen," and the number of medical image data "1" as fourth medical image data information.

Then, the operation screen generating unit 115e determines that a thumbnail icon image "head.jpeg" correlated with the imaging range "head" is used as an image to be attached to the surface of the thumbnail icon with respect to the first medical image data information by referring to the table illustrated in FIG. 10. Moreover, the operation screen generating unit 115e determines that "2" is selected as the stereoscopic effect of the thumbnail icon by referring to the table illustrated in FIG. 11. Moreover, the operation screen generating unit 115e acquires a group of parallax images in which a cuboid having the height corresponding to the stereoscopic effect "2" can be perceived stereoscopically and attaches the thumbnail icon image "head.jpeg" to each of the parallax images included in the group of parallax images.

Moreover, the operation screen generating unit 115e determines that a thumbnail icon image "head.jpeg" correlated with the imaging range "head" is used as an image to be attached to the surface of the thumbnail icon with respect to the second medical image data information by referring to the table illustrated in FIG. 10. Moreover, the operation screen generating unit 115e determines that "0" is selected as the stereoscopic effect of the thumbnail icon by referring to the table illustrated in FIG. 11. Moreover, the operation screen generating unit 115e acquires a rectangular planar image corresponding to the stereoscopic effect "0" and attaches the thumbnail icon image "head.jpeg" to the planar image.

Moreover, the operation screen generating unit 115e determines that a thumbnail icon image "abdomen.jpeg" correlated with the imaging range "abdomen" is used as an image to be attached to the surface of the thumbnail icon with respect to the third medical image data information by referring to the table illustrated in FIG. 10. Moreover, the operation screen generating unit 115e determines that "5" is selected as the stereoscopic effect of the thumbnail icon by referring to the table illustrated in FIG. 11. Moreover, the operation screen generating unit 115e acquires a group of parallax images in which a cuboid having the height corresponding to the stereoscopic effect "5" can be perceived stereoscopically and attaches the thumbnail icon image "abdomen.jpeg" to each of the parallax images included in the group of parallax images.

Moreover, the operation screen generating unit 115e determines that a thumbnail icon image "abdomen.jpeg" correlated with the imaging range "abdomen" is used as an image to be attached to the surface of the thumbnail icon with respect to the fourth medical image data information by referring to the table illustrated in FIG. 10. Moreover, the operation screen generating unit 115e determines that "0" is selected as the stereoscopic effect of the thumbnail icon by referring to the table illustrated in FIG. 11. Moreover, the operation screen generating unit 115e acquires a rectangular planar image corresponding to the stereoscopic effect "0" and attaches the thumbnail icon image "abdomen.jpeg" to the planar image.

Moreover, the operation screen generating unit 115e determines a region where respective thumbnail icons are arranged so that the first to fourth thumbnail icons are appropriately arranged in the thumbnail region on the optical screen. Here, the stereoscopic display monitor included in the medical image diagnostic apparatus 110 can display stereoscopic images by displaying a group of parallax images having a predetermined parallax number and can also display planar images by replacing a plurality of identical images with a group of parallax images and displaying the same. For example, as illustrated in FIG. 3, the stereoscopic display monitor according to the first embodiment can display stereoscopic images by outputting nine pixels of a 9-parallax image located at the same position by allocating the same to nine columns of pixels 202 and can also display planar images by outputting one pixel of the nine pixels by allocating the same to all of the nine columns of pixels 202.

Thus, for example, the operation screen generating unit 115e according to the first embodiment generates operation screen information so that the same pixels are allocated to all of the nine columns of pixels 202 with respect to a region of the operation screen other than the region where stereoscopic thumbnail icons or stereoscopic images are displayed. On the other hand, the operation screen generating unit 115e generates operation screen information so that nine pixels located at the same position in each of the parallax images included in a group of parallax images are allocated to the respective nine columns of pixels 202 with respect to the region of the operation screen where the stereoscopic thumbnail icons or stereoscopic images are displayed.

The above-described method of generating operation screen information is an example only. For example, an operation screen of a different layer may be generated for respective display regions, thumbnail regions, and thumbnail icons, the operation screens of respective layers may be subjected to necessary mask processing, and the respective processed layers may be disposed in a superimposed manner. In this case, the mask processing is performed such that the opacity of a region where information is disposed is set to 100%, and the opacity of a region where no information is disposed is set to 0%.

The display control unit 115f displays an operation screen on the display unit 112. Specifically, upon receiving the notification of generation of the operation screen display information from the operation screen generating unit 115e, the display control unit 115f acquires operation screen display information by referring to the operation screen information storage unit 114c. Moreover, the display control unit 115f displays an operation screen on the display unit 112 using the acquired operation screen display information, and if necessary, the medical image data stored in the medical image data storage unit 114b.

Figure 12:
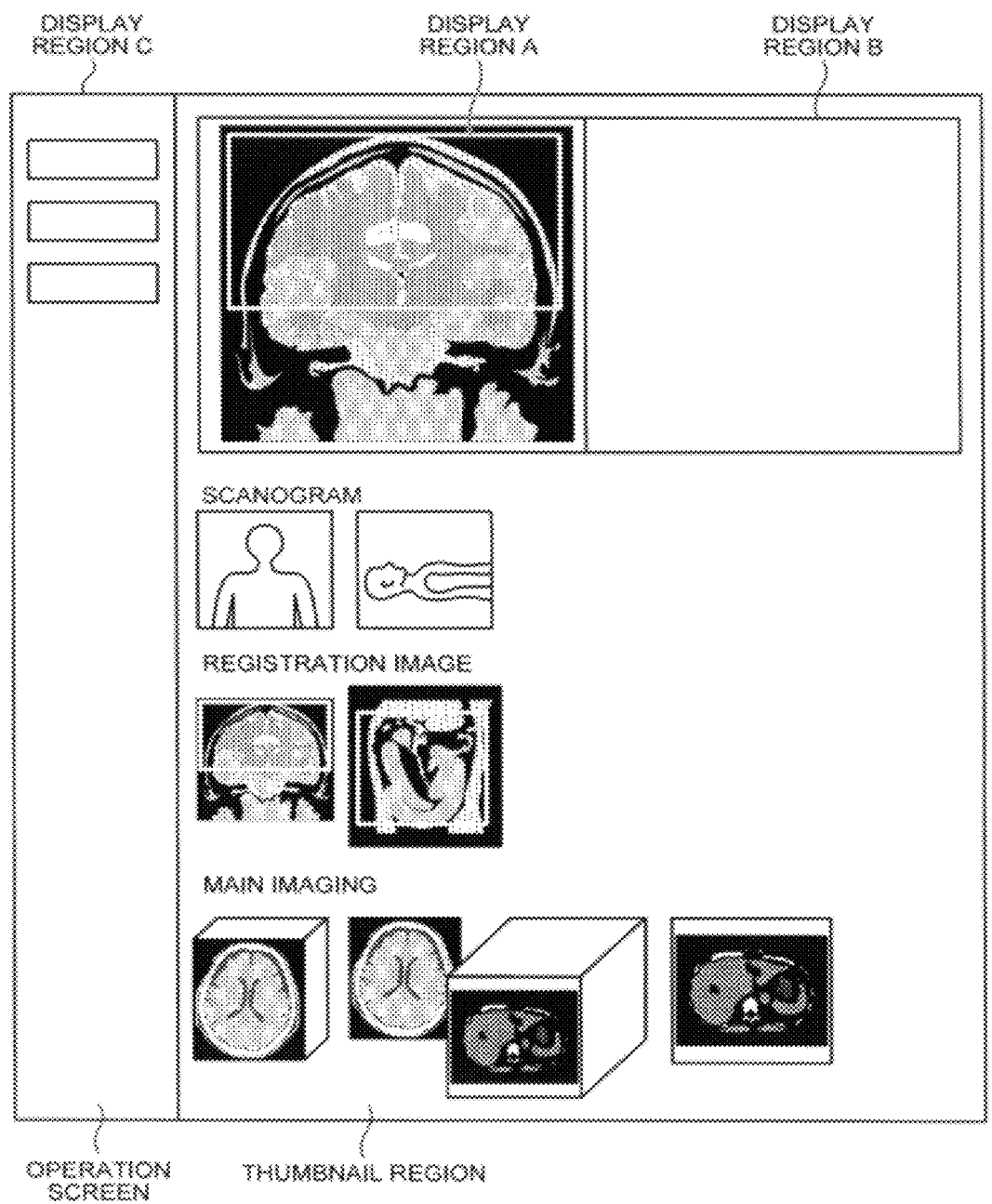
FIG. 12 is a diagram for describing an operation screen according to the first embodiment.

FIG. 12 is a diagram for describing an operation screen according to the first embodiment. The operation screen illustrated in FIG. 12 includes a display region A, a display region B, a display region C, and a thumbnail region. As illustrated in FIG. 12, the display region A is a region for displaying a registration image which is set in advance to be displayed on an initial screen. Moreover, for example, the display region B is a region for displaying a medical image corresponding to medical image data selected in a thumbnail region. For example, the display region C is a region for displaying the other sets of operation information. In the example illustrated in FIG. 12, a registration image corresponding to the head is displayed in the display region A, and nothing is displayed in the display region B.

Moreover, as illustrated in FIG. 12, the thumbnail region is a region for displaying thumbnail images. In the example illustrated in FIG. 12, thumbnail icons of medical image data collected by scanogram scanning, thumbnail icons of registration images, and thumbnail icons of medical image data collected by main imaging are displayed in the thumbnail region. The first to fourth thumbnail icons described above are displayed as "thumbnail icons of medical image data collected by main imaging" in the thumbnail region.

Moreover, the display control unit 115f updates the operation screen. Specifically, upon receiving the notification of the selected thumbnail icon from the operation receiving unit 115c, the display control unit 115f updates the operation screen in accordance with the selected thumbnail icon. For example, when the selected thumbnail icon means selecting certain volume data, the display control unit 115f displays a screen for receiving the input of rendering conditions for performing a rendering process using the volume data in another window different from the operation screen, for example. Moreover, for example, when the selected thumbnail icon means selecting a certain MPR image, the display control unit 115f acquires the MPR image from the medical image data storage unit 114b and displays the same in the display region B.

Figure 13:
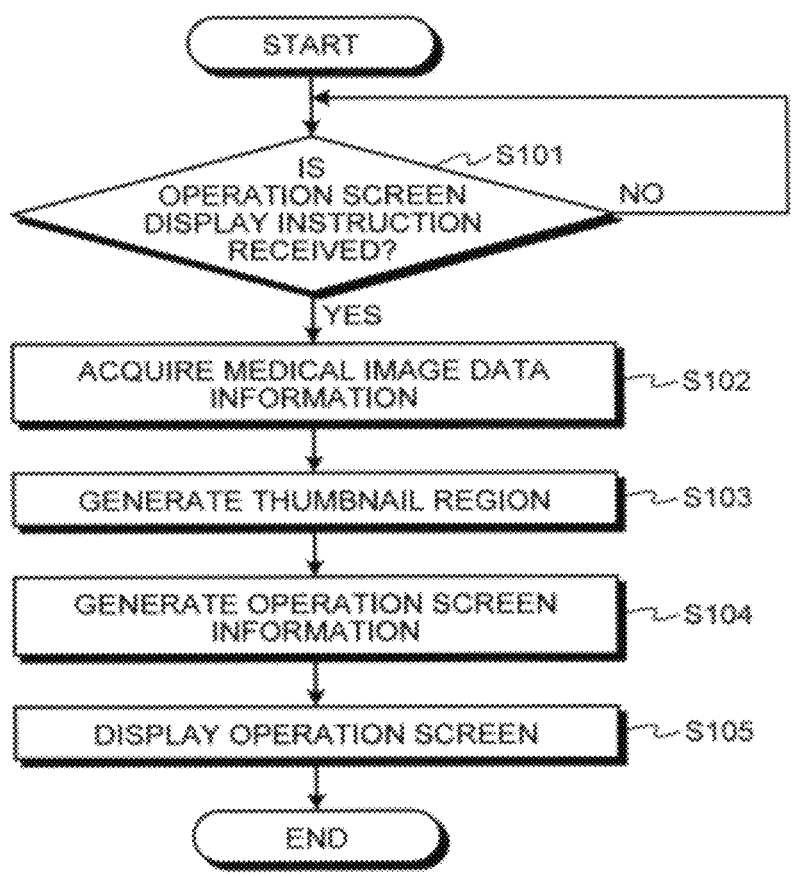
FIG. 13 is a flowchart illustrating the flow of a display control process according to the first embodiment.
Figure 14:
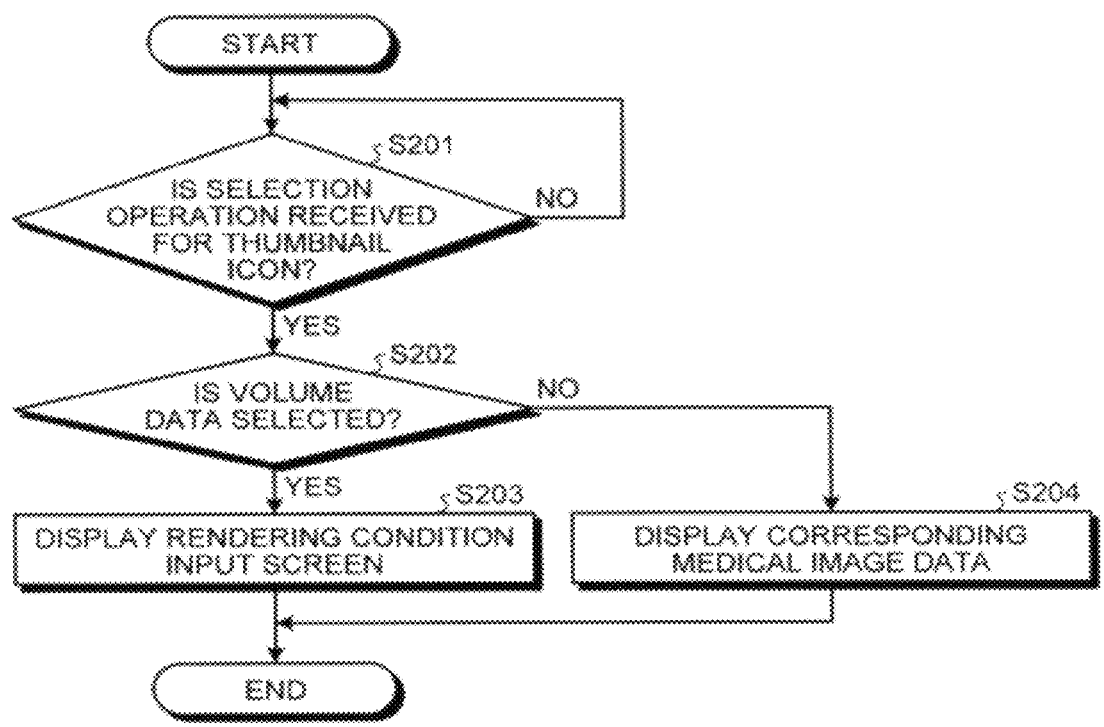
FIG. 14 is a flowchart illustrating the flow of a display control process according to the first embodiment.

Subsequently, FIGS. 13 and 14 are flowcharts illustrating the flow of a display control process according to the first embodiment. As illustrated in FIG. 13, when the operation receiving unit 115c receives an operation for an operation screen display instruction (Yes in step S101), the medical image data information acquiring unit 115d acquires medical image data information from the medical image data storage unit 114b (step S102). Subsequently, the operation screen generating unit 115e generates a thumbnail region (step S103) and generates operation screen display information (step S104). Moreover, the display control unit 115f displays an operation screen on the display unit 112 (step S105).

Moreover, as illustrated in FIG. 14, when the operation receiving unit 115c receives an operation of selecting a thumbnail icon (Yes in step S201), and the selected thumbnail icon means selecting volume data (Yes in step S202), the display control unit 115f displays a screen for receiving the input of rendering conditions in another window different from the operation screen, for example (step S203). On the other hand, when the selected thumbnail icon means selecting data other than volume data (No in step S202), the display control unit 115f acquires the corresponding medical image data from the medical image data storage unit 114b and displays the same in the display region B, for example (step S204).

Advantageous Effects of First Embodiment

As described above, according to the first embodiment, since whether thumbnail icons will be displayed as stereoscopic images or planar images is determined in accordance with the content of medical image data selected by the operator, the operation screen is displayed appropriately. Thus, the operator can understand the type of an image just by watching thumbnail icons. Moreover, according to the first embodiment, since medical image data is displayed so that the stereoscopic effect of thumbnail icons reflects the quantity of medical image data, the operation screen is displayed appropriately. Thus, the operator can understand the quantity of medical image data just by watching thumbnail icons.

Modification Example of First Embodiment

Next, a modification example of the first embodiment will be described. In the first embodiment, a method in which a thumbnail icon image corresponding to the imaging range is displayed to be attached to the surface of a cuboid as a thumbnail icon has been described. However, the embodiments are not limited to this.

In this modification example, a method of displaying a stereoscopic image generated by performing a rendering process on volume data as a thumbnail icon will be described.

Figure 15:
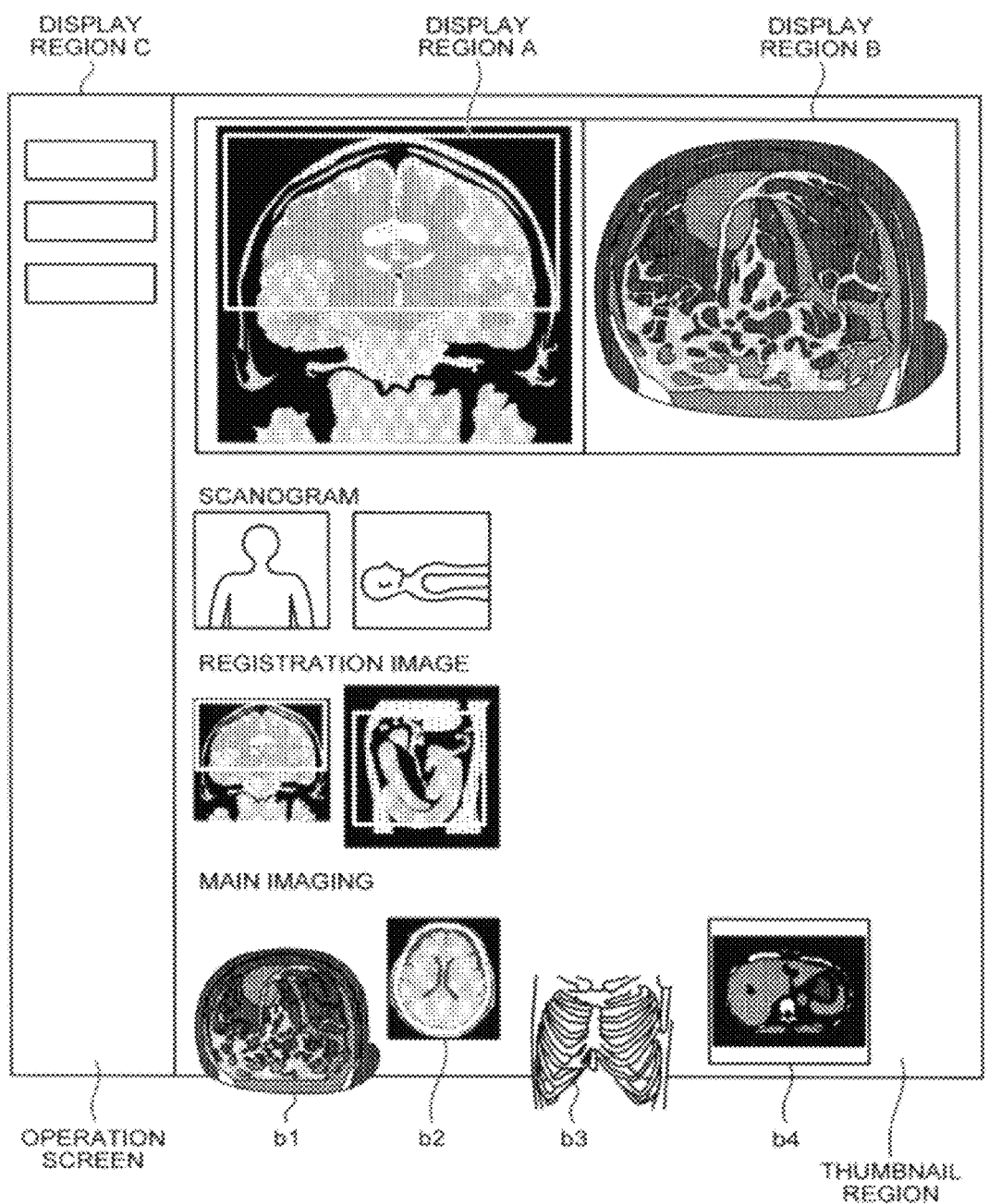
FIG. 15 is a diagram for describing an operation screen according to a modification example of the first embodiment.
Figure 16:
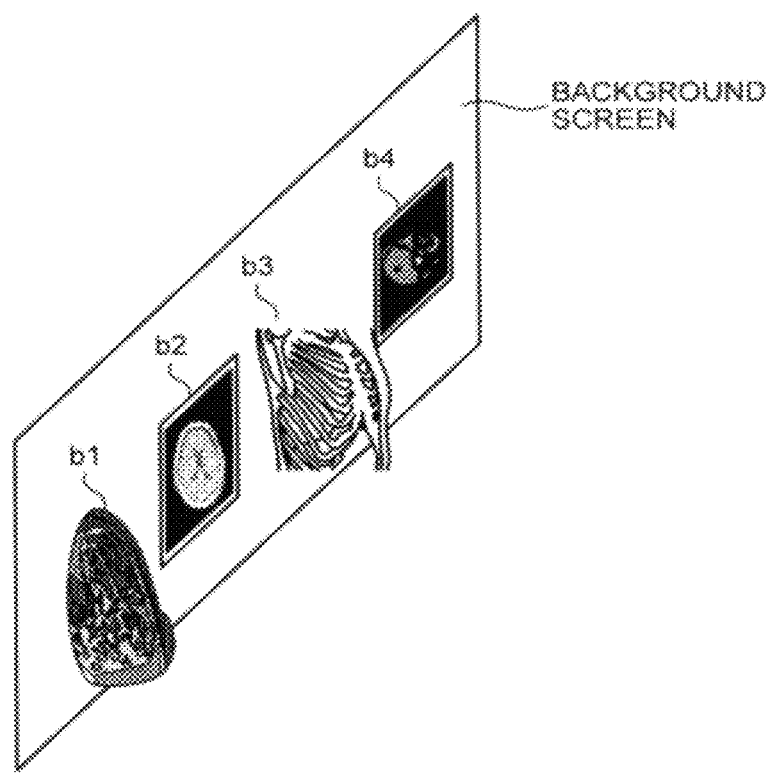
FIG. 16 is a diagram for describing an operation screen according to a modification example of the first embodiment.

FIGS. 15 and 16 are diagrams for describing an operation screen according to a modification example of the first embodiment. In FIG. 16, a part of a thumbnail region extracted from an operation screen is illustrated for the sake of convenience.

As illustrated in FIG. 15, the medical image diagnostic apparatus 110 displays thumbnail icons b1 and b3 as stereoscopic images and displays thumbnail icons b2 and b4 as planar images. Here, the thumbnail icons b1 and b3 illustrated in FIG. 15 are stereoscopic images generated by performing a rendering process on volume data. As illustrated in FIG. 16, for example, the thumbnail icon b1 is a stereoscopic image of brain blood vessels generated from the volume data of the head. Moreover, for example, the thumbnail icon b3 is a stereoscopic image of bones generated from the volume data of the abdomen.

Generation of thumbnail regions by the operation screen generating unit 115e according to this modification example will be described in detail. For example, the operation screen generating unit 115e receives the type of medical image data "volume data" and the imaging range in body axis direction "head" as first medical image data information. Moreover, the operation screen generating unit 115e receives the type of medical image data "MPR image" and the imaging range in body axis direction "head" as second medical image data information. Moreover, the operation screen generating unit 115e receives the type of medical image data "volume data"

and the imaging range in body axis direction "abdomen" as third medical image data information. Moreover, the operation screen generating unit 115e receives the type of medical image data "MPR image" and the imaging range in body axis direction "abdomen" as fourth medical image data information.

Then, since the type of medical image data for the first medical image data information is "volume data," the operation screen generating unit 115e determines to generate stereoscopic images and acquires the corresponding volume data by referring to the medical image data storage unit 114b. Moreover, in the first embodiment, it is set in advance that when generating stereoscopic images for thumbnail icons from the volume data of the imaging range "head," the operation screen generating unit 115e segments brain blood vessels and generates an image of the brain blood vessels. Moreover, the rendering conditions for generating stereoscopic images are set in advance. Thus, the operation screen generating unit 115e performs the rendering process by the rendering processing unit 116 with respect to the acquired volume data to thereby generate stereoscopic images, that is, a group of parallax images of the brain blood vessels. The operation screen generating unit 115e generates a group of parallax images so as to have the size of a region used as thumbnail icons.

Similarly, since the type of medical image data for the third medical image data information is "volume data," the operation screen generating unit 115e determines to generate stereoscopic images and acquires the corresponding volume data by referring to the medical image data storage unit 114b. Moreover, in the first embodiment, it is set in advance that when generating stereoscopic images for thumbnail icons from the volume data of the imaging range "abdomen," the operation screen generating unit 115e segments bones and generates an image of the bones. Moreover, the rendering conditions for generating stereoscopic images are set in advance. Thus, the operation screen generating unit 115e performs the rendering process by the rendering processing unit 116 with respect to the acquired volume data to thereby generate stereoscopic images, that is, a group of parallax images of the bones. The operation screen generating unit 115e generates a group of parallax images so as to have the size of a region used as thumbnail icons.

As for the second and fourth medical image data information, the operation screen generating unit 115e may generate thumbnail icons of planar images by the same method as the first embodiment. Moreover, similarly to the first embodiment described above, the operation screen generating unit 115e determines the region for arranging the respective thumbnail icons so that the first to fourth thumbnail icons are appropriately arranged in the thumbnail region on the operation screen and generates operation screen information so that the same pixels are allocated to all of the nine columns of pixels 202 with respect to region of the operation screen other than the region where the stereoscopic thumbnail icons and stereoscopic images are displayed. On the other hand, the operation screen generating unit 115e generates operation screen information so that nine pixels located at the same position in each of the parallax images included in a group of parallax images are allocated to the respective nine columns of pixels 202 with respect to the region of the operation screen where the stereoscopic thumbnail icons or stereoscopic images are displayed.

Other Modification Examples

Moreover, the embodiments are not limited to the above modification example. For example, in FIGS. 15 and 16, although thumbnail icons are arrange horizontally, the embodiments are not limited to this, but the thumbnail icons may be arranged vertically. For example, a thumbnail icon of "head," a thumbnail icon of "chest," a thumbnail icon of "abdomen," and a thumbnail icon of "leg" may be arranged vertically so that the imaging range can be understood immediately.

Moreover, a stereoscopic image which is a body mark prepared in advance may be displayed as a thumbnail icon, for example. In this case, the operation screen generating unit 115e stores the thumbnail icon b1 of FIG. 15 in advance as the thumbnail icon for the volume data of "head," for example, and stores the thumbnail icon b3 of FIG. 15 in advance as the thumbnail icon of the volume data of "abdomen," for example. Moreover, the operation screen generating unit 115e may select the corresponding thumbnail icon based on medical image data information and display the thumbnail icon.

Second Embodiment

Next, a second embodiment will be described. Although thumbnail icons are displayed so as to be perceived stereoscopically in the first embodiment, a message notified to an operator is displayed so as to be perceived stereoscopically in the second embodiment.

From the past, the medical image diagnostic apparatus 110 has displayed a message notified to the operator on the operation screen using characters, a pop-up window, or the like. However, if the message is displayed as characters or a pop-up window, the operator may miss the presence thereof.

In this regard, the medical image diagnostic apparatus 110 according to the second embodiment determines whether the message will be displayed as a stereoscopic image or as a planar image depending on the content of the message. That is, when the message notified to the operator is set as a message of high importance, the medical image diagnostic apparatus 110 displays the message as a stereoscopic image. As a result, the operation screen is displayed appropriately so that medical information that should attract the operator's attention appears prominent, and the operator cannot miss the message of high importance. This will be described below.

Figure 17:
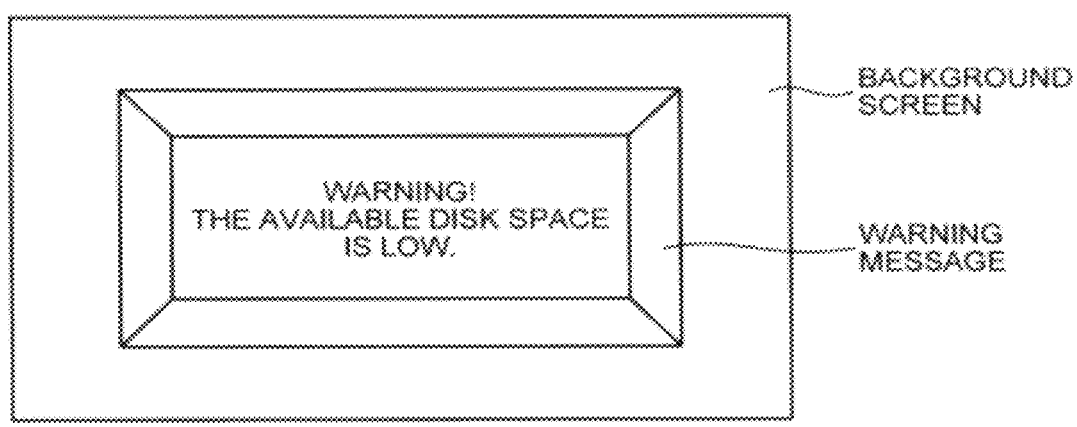
FIG. 17 is a diagram for describing a display example according to a second embodiment.

FIG. 17 is a diagram for describing a display example according to the second embodiment. As illustrated in FIG. 17, the medical image diagnostic apparatus 110 displays a warning message as a stereoscopic image, for example. Although the stereoscopic effect of the stereoscopic image in the second embodiment means the sense of frontward protrusion from a reference surface (the background screen in FIG. 17) of the operation screen, the embodiments are not limited to this, but the stereoscopic effect may be the sense of depth in the depth direction from the reference surface or a combination of the sense of protrusion and the sense of depth.

For example, the medical image diagnostic apparatus 110 stores various types of messages and the importance thereof in advance in correlation. Moreover, upon receiving a message display instruction from the imaging unit 115a or the reconstructing unit 115b, for example, the display control unit 115f controls so that the message is displayed as a stereoscopic image by referring to the importance stored in correlation with the message when the importance thereof exceeds a predetermined threshold value. For example, the display control unit 115f instructs the operation screen generating unit 115e to generate the stereoscopic image of the message, and the operation screen generating unit 115e generates a stereoscopic image and sends the stereoscopic image to the display control unit 115f. Then, the display control unit 115f displays the stereoscopic image in another layer different from the layer in which the operation screen is displayed, for example, and displays the layer of the operation screen and the layer of the stereoscopic image in a superimposed manner. Similarly to the thumbnail icon described in the first embodiment, the operation screen generating unit 115e may generate a stereoscopic image by attaching a message to a group of parallax images for messages generated in advance by performing computation processing so that a cuboid can be perceived stereoscopically, for example. Alternatively, such a stereoscopic image may be prepared in advance for each message.

Threshold values may be provided in steps so that the stereoscopic effect reflects the degree of importance. For example, the stereoscopic effect may be increased as the importance of a message increases. Moreover, the color may reflect the degree of importance. For example, the message is displayed "red" for the importance of a high level, "yellow" for the importance of a middle level, and "green" for the importance of a low level. For example, the operation screen generating unit 115e may store a group of parallax images for respective stereoscopic effects and colors in advance and generate a stereoscopic image by reading the group of parallax images and attaching a message to the same.

A specific example will be described. For example, it is assumed that the medical image diagnostic apparatus 110 is in a state where it has a low available disk space for storing medical image data. Moreover, it is assumed that a message "Warning! The available disk space is low" is prepared in advance as the information for informing the operator of such a state, and high importance is set to the message.

Then, for example, upon receiving a message display instruction from the reconstructing unit 115b, the display control unit 115f specifies that the importance of the message exceeds a threshold value by referring to the importance thereof. Moreover, the display control unit 115 instructs the operation screen generating unit 115e to generate a stereoscopic image of a message "Warning! The available disk space is low," and the operation screen generating unit 115e generates a stereoscopic image and sends the stereoscopic image to the display control unit 115f. Then, the display control unit 115f displays a stereoscopic message "Warning! The available disk space is low." on the operation screen.

Whether the message will be displayed as a stereoscopic image may be determined depending on the stage where the message is notified, for example, as well as the warning level. For example, it is assumed that the message "Warning! The available disk space is low." is likely to be notified in two stages of an imaging planning stage and an imaging stage. When this message is notified in the imaging planning stage, this message is notified via a sound in addition to characters and a pop-up window. On the other hand, when this message is notified in the imaging stage, the message is not notified via a sound from consideration of patients. Therefore, although the display control unit 115f does not display the message as a stereoscopic image in the imaging planning stage where a notification is performed via a sound, the display control unit 115f displays the message as a stereoscopic image in an imaging stage where the notification is not performed via a sound.

Advantageous Effects of Second Embodiment

As described above, according to the second embodiment, since whether the message will be displayed as a stereoscopic image or a planar image is determined depending on the content of the message, the operation screen is displayed appropriately. Thus, the operator cannot miss a message of high importance.

Other Embodiments

Several other embodiments will be described.

Hereinabove, although an example in which thumbnail icons are displayed so as to be perceived stereoscopically has been described in the first embodiment, and an example in which a message to be notified to the operator is displayed so as to be perceived stereoscopically has been described in the second embodiment, the embodiments are not limited to this. For example, the medical image diagnostic apparatus 110 displays an imaging planning screen when planning imaging, and the imaging planning screen may be controlled to be displayed as a stereoscopic image or a planar image depending on the content of the imaging planning screen. For example, although the medical image diagnostic apparatus 110 according to a third embodiment displays a normal imaging planning screen as a planar image, when displaying a graph (hereinafter referred to as a time schedule screen) for planning execution of various imaging protocols as an imaging planning screen, the medical image diagnostic apparatus 110 displays the time schedule screen as a stereoscopic image.

FIG. 18 is a diagram for describing a time schedule screen according to the third embodiment. As illustrated in FIG. 18, a graph for creating a rod graph for each imaging protocol using a time axis (the axis of imaging in FIG. 18) as the horizontal axis is displayed on the time schedule screen. The operator can determine the type of an imaging protocol performed in an examination, the order thereof, and the like by inputting operations on the graph. For example, "RP" illustrated in FIG. 18 means "real time prep" imaging. For example, when the operator clicks on "RP" on the time schedule screen and draws a rectangle at an optional position on the graph, it is planned that "real time prep" imaging is performed at the time indicated by the position where the rectangle is drawn.

Here, for example, when generating the time schedule screen within the imaging planning screen, the operation screen generating unit 115e generates a graph of which the horizontal axis is "axis of image processing" in addition to the graph of which the horizontal axis is "axis of imaging" and generates operation screen information so that these graphs are displayed in a superimposed manner so as to be perceived stereoscopically as illustrated in FIG. 18. In FIG. 18, although the graph of which the horizontal axis is "axis of image processing" is illustrated to be shifted for the sake of convenience, actually the graph of which the horizontal axis is "axis of image processing," for example is displayed with the sense of protrusion or the sense of depth. The operator can designate image data to be subjected to image processing by inputting operations on the graph for image processing. For example, when the operator draws a rectangle a on the "axis of image processing," it is planned that three sets of volume data at the center among dynamic volume data collected in five sets are subjected to image processing.

The graph of which the horizontal axis is "axis of image processing" may not be displayed always, and may be displayed when the operator presses a button indicating "to display "axis of image processing"," for example. For example, the operation screen generating unit 115e may generate operation screen information for displaying as a planar image and generate operation screen information for displaying as a stereoscopic image depending on whether this button is pressed or not.

Moreover, the embodiment is not limited to the above-described embodiments, but "axis of imaging" of which the horizontal axis is the time axis may be prepared for each imaging protocol, and the respective axes may be arranged in the vertical direction to the display surface with the sense of protrusion or the sense of depth. In this way, it is possible to obtain an advantage effect that the operator can easily perceive the "axis of imaging" for each imaging protocol.

In the above-described embodiment, although the operation screen of the medical image diagnostic apparatus 110 has been described by way of an example, the embodiments are not limited to this. For example, the same can be applied to the operation screen of the workstation 130 or the operation screen of the terminal device 140. In this case, the workstation 130 or the terminal device 140 has the functions corresponding to the storage unit 114, the control unit 115, and the rendering processing unit 116. Moreover, when the workstation 130 or the terminal device 140 acquires medical image data archived in the image archiving device 120 in accordance with the DICOM standard and displays an operation screen, additional information of DICOM can be used as "medical image data information" described in the above-described embodiments, for example.

Moreover, in the above-described embodiment, the terminal device 140 has been described to display the medical images and the like acquired from the image archiving device 120. However, the embodiments are not limited to this. For example, the terminal device 140 may be directly connected to the medical image diagnostic apparatus 110.

Moreover, in the above-described embodiment, although 9-parallax images have been described by way of an example, the embodiments are not limited to this, and an optional parallax number such as two parallaxes or six parallaxes may be used, for example. Moreover, all of the design of the operation screen, the number of thumbnail icons, the method of aligning thumbnail icons, the shape of thumbnail icons, the design of a stereoscopic message can be change in an optional way.

Others

Respective constituent elements of respective apparatuses illustrated in the drawings are functionally conceptual, and physically the same configuration illustrated in the drawings is not always necessary. That is, the specific forms of distribution and integration of the devices are not limited to the illustrated forms, and all or a part thereof can be functionally or physically distributed or integrated in an arbitrary unit, according to various kinds of load and the status of use. Furthermore, all or an arbitrary part of the processing functions performed by the respective apparatuses can be realized by a CPU and a program analyzed and executed by the CPU, or can be realized as hardware by a wired logic.

Moreover, the image processing method described in the above embodiments can be realized when an image processing program prepared in advance is executed by a computer such as a personal computer or a workstation. The image processing program may be distributed via a network such as the Internet. Moreover, this program may be executed by being recorded in a computer-readable recording medium such as a hard disk, a flexible disk (FD), a CD-ROM, a MO, or a DVD, and read from the recording medium by a computer.

According to the image processing system and method of at least one of the embodiments described herein above, it is possible to display the operation screen appropriately.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing system comprising:
a display capable of displaying stereoscopic images by displaying a plurality of groups of parallax images; and
a processor configured to display an operation screen for receiving operations on medical image data on the display, display a thumbnail image for each of the respective groups of parallax images, for selecting the medical image data on the operation screen, and control whether the thumbnail image will be displayed as a stereoscopic image or a planar image depending on the content of the medical image data selected by the thumbnail image, wherein
the processor increases a parallax angle of each respective group of parallax images for displaying the thumbnail image in accordance with a number of images included in the medical image data, and
when the thumbnail image is displayed as a stereoscopic image, the processor displays the thumbnail image so that stereoscopic effect of the thumbnail image increases as the number of the medical image data increases.

2. The image processing system according to claim 1, wherein
when the thumbnail image is displayed as the stereoscopic image, the processor uses a group of parallax images generated by performing a rendering process on the 3-dimensional medical image data.

3. The image processing system according to claim 1, wherein
when the thumbnail image is displayed as the stereoscopic image, the processor uses a group of parallax images generated by performing a rendering process on the 3-dimensional medical image data.

4. The image processing system according to claim 1, wherein
the processor displays an operation screen for receiving operations of an operator on the display, displays notification information to be notified to the operator on the operation screen, and controls whether the notification information will be displayed as a stereoscopic image or a planar image depending on the content of the notification information.

5. An image processing method executed by an image processing system, comprising:
displaying an operation screen for receiving operations on medical image data on a display capable of displaying stereoscopic images by displaying a plurality of groups of parallax images, each displaying a respective thumbnail image for selecting the medical image data on the operation screen, and specifying whether the thumbnail image will be displayed as a stereoscopic image or a planar image depending on the content of the medical image data selected by the thumbnail image; and
increasing a parallax angle of each respective group of parallax images for displaying the thumbnail image in accordance with a number of images included in the medical image data, and when the thumbnail image is displayed as a stereoscopic image, the processor displays the thumbnail image so that stereoscopic effect of the thumbnail image increases as the number of the medical image data increases.

6. The image processing method executed according to claim 5, further comprising:

displaying notification information to be notified to the operator on the operation screen, and specifying whether the notification information will be displayed as a stereoscopic image or a planar image depending on the content of the notification information; and controlling so that the notification information is displayed on the display.

* * * * *